US009383424B2

(12) United States Patent
Gulaka et al.

(10) Patent No.: US 9,383,424 B2
(45) Date of Patent: Jul. 5, 2016

(54) SYSTEM AND METHOD FOR AUTOMATIC PLANNING OF VIEWS IN 3D IMAGES OF BRAIN

(71) Applicant: SAMSUNG ELECTRONICS CO., LTD., Suwon-si (KR)

(72) Inventors: Praveen Gulaka, Moscow (RU); Alexey Bronislavovich Danilevich, Moscow (RU); Mikhail Yurievich Sirotenko, Moscow (RU); Dmitry Alexandrovich Korobchenko, Moscow (RU); Mikhail Nikolaevich Rychagov, Moscow (RU); Sergey Konstantinovich Ternovoy, Moscow (RU); Merab Archil'evich Sharia, Moscow (RU); Dmitry Vladimirovich Ustuzhanin, Moscow (RU)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 170 days.

(21) Appl. No.: 14/218,028

(22) Filed: Mar. 18, 2014

(65) Prior Publication Data

US 2014/0270434 A1    Sep. 18, 2014

(30) Foreign Application Priority Data

Mar. 18, 2013   (RU) ................................ 2013111935

(51) Int. Cl.
  *G01R 33/54*    (2006.01)
  *A61B 5/055*    (2006.01)
  (Continued)

(52) U.S. Cl.
  CPC ............ *G01R 33/543* (2013.01); *A61B 5/0037* (2013.01); *A61B 5/055* (2013.01); *G06K 9/20* (2013.01); *G06T 7/0012* (2013.01); *G06T 2207/10088* (2013.01); *G06T 2207/30016* (2013.01)

(58) Field of Classification Search
  None
  See application file for complete search history.

(56) References Cited

U.S. PATENT DOCUMENTS 7,450,983 B2   11/2008   Weiss
8,002,019 B2    8/2011   Min et al.
(Continued)

OTHER PUBLICATIONS

Wang D et al, "Automated detection of mid-sagittal plane in MR images of the head", Proceedings of SPIE; Medical Imaging 2001: Image Processing, SPIE—International Society for Optical Engineering, US; San Diego, CA, USA, vol. 4322, Jan. 1, 2001, pp. 1243-1253, XP008169442, English / Cited in EP Comm. Jun. 3, 2014 in 14160598.0.

(Continued)

*Primary Examiner* — Siamak Harandi
(74) *Attorney, Agent, or Firm* — Sughrue Mion, PLLC

(57) ABSTRACT

A method of automatic planning of a view in a 3D image of a brain includes A method of automatic planning a view in a three-dimensional (3D) image of a brain includes selecting a plurality of axial working sections and a plurality of coronal working sections in the 3D scout image; constructing at least one mid-sagittal plane of the brain based on a set of axial reference lines and a set of coronal reference lines obtained from the selected plurality of axial working sections and the selected plurality of coronal working sections, respectively; detecting at least one landmark that is an anatomical point in the at least one mid-sagittal plane; creating a first reference line based on the at least one landmark detected in the at least one mid-sagittal plane; and planning a scan in an orientation based on the at least one mid-sagittal plane and the first reference line.

15 Claims, 20 Drawing Sheets

(51) Int. Cl.
*G06K 9/20* (2006.01)
*G06T 7/00* (2006.01)
*A61B 5/00* (2006.01)

(56) References Cited

U.S. PATENT DOCUMENTS

| | | |
|---|---|---|
| 8,190,232 B2 | 5/2012 | Zhang et al. |
| 8,270,698 B2 | 9/2012 | Geiger |
| 2008/0071163 A1 | 3/2008 | Zhang et al. |
| 2009/0093706 A1 | 4/2009 | Zhang et al. |
| 2010/0172566 A1 | 7/2010 | Goto |
| 2012/0093384 A1 | 4/2012 | Goto et al. |
| 2012/0093385 A1 | 4/2012 | Yokosawa et al. |

OTHER PUBLICATIONS

Liu, Yanxi; et al., "Robust midsagittal plane extraction from normal and pathological 3-D neuroradiology images", 0278-0062/01, IEEE Trans. Med. Imag., vol. 20, No. 3 Mar. 2001, pp. 175-192, XP002724831, Retrieved from the Internet: URL: http://ieeexplore.ieee.org/stamp/stamp.jsp?arnumber=00918469, English / Cited in EP Comm. Jun. 3, 2014 in 14160598.0.

Communication from the European Patent Office issued Jun. 3, 2014 in a counterpart European Application No. 14160598.0.

FIG. 19A    FIG. 19B    FIG. 19C
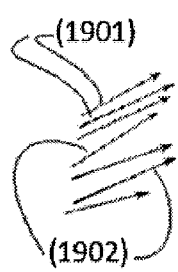
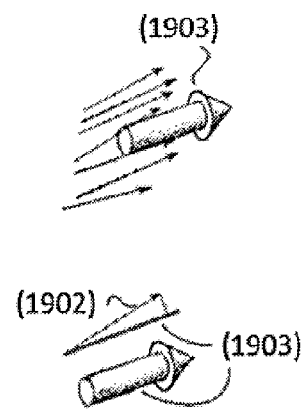
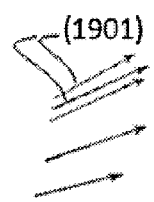
FIG. 20
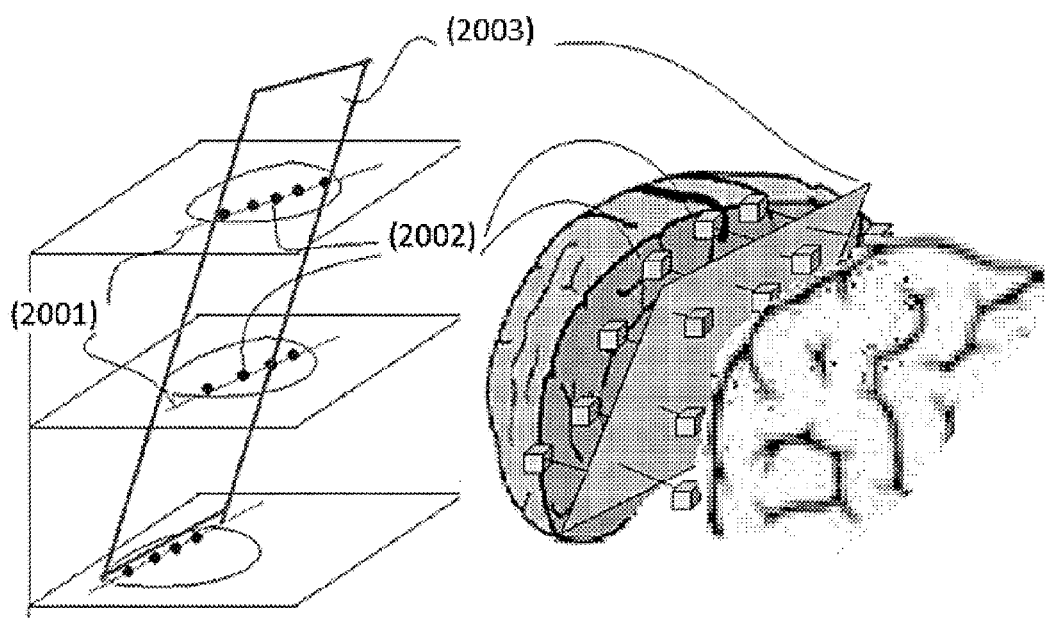

SYSTEM AND METHOD FOR AUTOMATIC PLANNING OF VIEWS IN 3D IMAGES OF BRAIN

RELATED APPLICATIONS

This application claims priority from Russian Patent Application No. 2013111935, filed on Mar. 18, 2013, in the Russian Patent Office, the disclosure of which is incorporated herein in its entirety by reference.

BACKGROUND

1. Field

Apparatuses and methods consistent with exemplary embodiments relate to medical equipment, and more particularly, to automatic planning of views in three-dimensional (3D) images of a brain.

2. Description of the Related Art

Medical images acquired by a medical imaging technique, e.g., magnetic resonance tomography (MRT), are widely used in modern diagnostic researches, particularly in researches of a human brain. Qualitative planning of views, also known as planning of scans, has higher importance for visualization of images of an object and correcting diagnosis settings.

Anatomical structures needs to be considered for planning views, i.e., the planned views needs be provided according to anatomical criteria including, for example, existing reference lines, axes and symmetry planes. In particular, in brain researches, standard positions in a plane dividing two hemispheres (i.e., passing through a longitudinal cleft of the brain, also called a longitudinal fissure) are used for a sagittal view, and various standard axial (or transverse) views constructed on stipulated anatomical points are used as a longitudinal plane of symmetry. For example, the standard axial views may be construed according to orientation in Talairach's space.

A procedure of planning of views of a brain may require significant time when manually executed. Planning of views refers to generation of an image having a predetermined cross-section based on a 3D scout image. Moreover, in manual planning, highly qualified medical personnel may spend significant time and energy in a routine operation for performing manual planning. Efficiency of a brain scan may be increased by applying an automatic procedure of planning of views based on the analysis of 3D scout images. Hereinafter, a scout image is understood as a preliminary 3D picture provided for the purpose of localization of area of interest.

Requirements for planning of views for medical images using standard anatomical landmarks, reference lines, and symmetry planes are well known.

Thus, methods of automatic planning of views have been developed. It is desirable that methods of automatic planning of views are performed at a higher speed and reliable (or robust) for use of scout images of lower resolution because the scout images may be often obtained at a preliminary stage together with a view of process acceleration. Much research has been conducted to solve the above task. In general, a mid-sagittal plane (MSP) is used as a natural plane of symmetry and for creating a longitudinal reference axis, which provide anatomical landmarks for this plane. In this regard, most approaches are similar to each other, with differences in methods of searching for reference lines and planes.

Some methods provide aspects related to specific parts of planning of views. For example, U.S. Pat. No. 7,450,983 describes determination of anatomical structures of a brain as connection of anterior and posterior commissures in mid-sagittal planes (MSPs); U.S. Pat. No. 7,986,823 describes determination of an MSP as a separate task; and U.S. Pat. Nos. 8,002,019, 8,190,232 and 8,270,698 also discuss construction of an MSP and search of anatomical landmarks therein.

U.S. Pat. Nos. 7,450,983 and 8,002,019 describe a faster and economical method for searching reference lines to construct an MSP, in which two reference lines detected in sections are used for MSP construction. Such an approach does not show a higher robustness since the method does not process a redundant set of sections. Furthermore, use of lower resolution scout images may lead to unreliable construction of an MSP because of statistical instability of the used data.

U.S. Pat. No. 8,270,698 presents a method of processing of a redundant set of axial sections for MSP construction, which may significantly increase robustness of the method. However, this method uses only axial sections without considering a coronal section. Hence, useful additional information on the coronal section is not used in this method. That is, in this method, working sections are selected without using anatomical features of a brain, and thus, a set of working sections is obtained by simple uniform "chopping" of the whole image from the bottom to the top. Thus, in this method, no preliminary stage of a process for efficient selection of working sections is provided. Robustness of the approach may be increased if processing of coronal sections along with axial sections is provided and a specific procedure implementing a preliminary selection of working sections takes into consideration anatomical features of a brain. There is no preliminary selection of sections in the approach presented by U.S. Pat. No. 7,986,823, which uses only two working sections: a first section (or axial cut) is selected simply as an average layer of the whole 3D scout image.

In U.S. Pat. Nos. 7,450,983 and 8,270,698, an approximate ellipse is constructed and its properties of symmetry are used in processing of sections for detection of a middle line therein. In U.S. Pat. No. 8,270,698, an elliptical mask of a section is constructed by preliminarily selected contour of an image of a brain. The approach is more reliable in which a mask covering the real form of a cut of a brain in a section is used instead of an ellipse encircling a contour. Major axes of such a plane figure may differ from axes of a contour ellipse. Furthermore, at lower resolution of a scout image, a construction of the plane figure covering a section is more statistically reliable than selection of a contour of the section and construction of an ellipse on the contour.

U.S. Pat. Nos. 8,002,019 and 8,190,232 relate to detection of a middle line in sections. Lines of symmetry of approximate ellipses are used only at an initial stage, and detailed stages are applied during which a position of a dark line dividing cerebral hemispheres is detected. Gradient masks are used to detect dark pixels. However, in a real embodiment, detection may be complicated because a desired line may have rather complex properties. The complexity of detection depends on the position of a selected section relative to an anatomical structure of the whole brain and quality of the scout image. For example, the detected line may be discontinuous, non-uniform in intensity of pixels, and have distributed characteristics, which means that the detected line has complicated properties than when a detected local gradient mask is concentrated.

A special numerical criterion for detecting a trace of a longitudinal cleft of a brain (or fissure) in a set area of a section may be used to improve effectiveness of the method. In a certain case, a line that divides cerebral hemispheres may be darker; however, other variants of intensity of pixels that cause such a dark line may exist. For example, the variants of intensity of pixels may depend on a method or protocol used for reception of an image.

In U.S. Pat. Nos. 7,450,983, 8,002,019 and 8,190,232, since only two reference lines are used for construction of an MSP, a post-processing for filtration of the unreliable (or untenable) data is not applied. In the Patent [5], redundant data are used, and consequently the MSP is constructed using a regressive method (i.e., auxiliary reference points are created based on received reference lines, and the required plane is constructed on a set of the points). This approach may increase robustness, but a post-processing for filtration of statistically unreliable reference lines is not applied.

Filtering statistically unreliable reference lines demonstrates a higher reliability. For example, it is possible to delete lines whose direction vector significantly differs from a generalized direction of the whole set of reference lines.

SUMMARY

One or more exemplary embodiments provide a system and method for automatic planning of views in three-dimensional (3D) images of a brain, which are capable of processing both higher and lower resolution images with improved reliability (or robustness).

One or more exemplary embodiments also provide a non-transitory computer-readable storage medium storing a program for executing the method by a computer.

According to an aspect of an exemplary embodiment, there is provided a method of automatic planning of a view in a three-dimensional (3D) image of a brain including: acquiring a 3D scout image; selecting a plurality of axial working sections and a plurality of coronal working sections in the 3D scout image; constructing at least one mid-sagittal plane of the brain based on a set of axial reference lines and a set of coronal reference lines obtained from the selected plurality of axial working sections and the selected plurality of coronal working sections, respectively; detecting at least one landmark that is an anatomical point in the at least one mid-sagittal plane; creating a first reference line based on the at least one landmark detected in the at least one mid-sagittal plane; and planning a scan in an orientation based on the at least one mid-sagittal plane and the first reference line.

The set of axial reference lines and the set of coronal reference lines may be obtained by using a numerical criterion that is calculated based on pixels in the plurality of axial working sections and the plurality of coronal working sections, the pixels being selected by analysis of the 3D scout image and based on detection of traces of a longitudinal fissure of the brain in the plurality of axial working sections and the plurality of coronal working sections, and constructed by filtering, from the set of axial reference lines and the set of coronal reference lines, a set of lines which are incompatible in a direction with a generalized vector having a direction of all lines in the set of axial reference lines and the set of coronal reference lines.

The creating the first reference line may include determining a detector for detecting a longitudinal fissure of the brain, the detector comprising a set of pixels that are used for calculating the numerical criterion at a position of the detector; creating a binary mask defined by an area of a two-dimensional (2D) image of the brain in at least one of the plurality of axial working sections and the plurality of coronal working sections; obtaining main axes of the binary mask; selecting a working area for detecting the longitudinal fissure of the brain in the at least one of the plurality of axial working sections and the plurality of corona working sections based on a geometrical structure of the binary mask and setting at least one parameter for changing a position of the detector in the working area, wherein the at least one parameter comprises a range of at least one from among coordinates and an angle of rotation of the detector; determining a desired position of the detector in the working area based on the numerical criterion; and calculating the first reference line in the working area based on a central axis of the detector at the desired position.

The determining the detector for detecting the longitudinal fissure of the brain may include detecting the longitudinal fissure of the brain in a form of a band having a discontinuous part, the discontinuous part being excluded for calculating the numerical criterion.

The numerical criterion may be calculated based on comparison between intensities of the pixels in the plurality of axial working sections and the plurality of coronal working sections and a predetermined threshold value.

The numerical criterion may be calculated based on a normalized weighted sum of intensities of the pixels.

The numerical criterion may be calculated based on a normalized weighted sum of intensities of pixels of which intensities are in a predefined range.

The determining the detector may include determining the detector based on detecting the longitudinal fissure of the brain at predefined positions of the detector.

The determining the detector may include determining the detector based on a bundle of a plurality of lines selected from among a set of secants that are substantially parallel with one another, and the detecting the longitudinal fissure of the brain may be performed at predefined directions of secants of the set of scants.

The constructing the at least one mid-sagittal plane of the brain based on the set of axial reference lines and the set of coronal reference lines may include obtaining a vector having a generalized direction of axial reference lines of the set of axial reference lines; obtaining boundary points of the axial reference lines of the set of axial reference lines based on points of intersection between lines providing borders of binary masks corresponding to the plurality of axial working sections; obtaining a central point having coordinates determined based on averaged coordinates of the boundary points; constructing a plane that is orthogonal to the vector and passes through the central point; determining points of intersection between the reference lines of the set of axial reference lines and creating a set of the points of intersection; constructing a reference line based on a regression straight line passing through the set of the points of intersection; and constructing the at least one mid-sagittal plane based on a plane in which a normal vector is orthogonal to the vector and the reference line and passing through the central point.

The constructing the at least one mid-sagittal plane of the brain based on the set of axial reference lines and the set of coronal reference lines may include obtaining a first vector having a generalized direction of axial reference lines of the set of axial reference lines; obtaining boundary points of the axial reference lines of the set of axial reference lines based on points of intersection between lines providing borders of binary masks corresponding to the plurality of axial working sections; obtaining a central point having coordinates determined based on averaged coordinates of the boundary points; constructing a plane that is orthogonal to the first vector and passes through the central point; determining points of intersection between the reference lines of the set of axial reference lines and creating a set of the points of intersection; constructing a reference line based on a regression straight line passing through the set of the points of intersection; obtaining a second vector having a generalized direction of coronal reference lines of the set of coronal reference lines; obtaining a third vector based on a weighted sum of the second vector and the reference line; and constructing the at least one mid-sagittal plane as a plane in which a normal vector is orthogonal to the first vector and the third vector and passing through the central point.

The constructing the at least one mid-sagittal plane of the brain based on the set of axial reference lines and the set of coronal reference lines may include obtaining boundary points that are points of intersection between lines in the set of axial reference lines and edges of binary masks corresponding to the plurality of axial working sections; obtaining boundary points that are points of intersection between lines in the set of coronal reference lines and edges of binary masks corresponding to the plurality of coronal working sections; and obtaining the at least one mid-sagittal plane based on a regression plane comprising the boundary points using a least square method.

According to an aspect of still another exemplary embodiment, provided is a system for automatically planning a view in a three-dimensional (3D) image of a brain, the system including: a 3D scout image providing block configured to collect data of a medical image, and provide a 3D scout image from the data of the medical image; a working section selection block configured to analyze the 3D scout image provided by the 3D scout image providing block, and select a plurality of axial working sections and a plurality of coronal working sections; an axial section reference line calculation block configured to analyze the plurality of axial working sections selected by the working section selection block, detect traces of a longitudinal fissure of the brain in the plurality of axial working sections, and compute a set of axial reference lines based on central axial lines of the detected traces; a coronal section reference line calculation block configured to analyze the plurality of coronal working sections selected by the working section selection block, detect traces of a longitudinal fissure of the brain in the plurality of coronal working sections, and compute a set of coronal reference lines based on central coronal lines of the detected traces; an axial reference line filtration block configured to filter the set of axial reference lines computed by the axial section reference line calculation block by excluding, from the set of axial reference lines, lines whose direction vector differs from a vector having a generalized direction of the set of the axial reference lines by a certain degree, and provide a filtered set of axial reference lines; a coronal reference line filtration block configured to filter the set of coronal reference lines computed by the coronal section reference line calculation block by excluding, from the set of coronal reference lines, lines whose direction vector differs from a vector having a generalized direction of the set of the coronal reference lines by the certain degree, and provide a filtered set of coronal reference lines; a mid-sagittal plane (MSP) calculation block configured to provide a plane by applying a least square method to the filtered set of axial reference lines provided by axial reference line filtration block and the filtered set of coronal reference lines provided by the coronal reference line filtration block, and provide parameters of the plane; an MSP image reconstruction block configured to provide an MSP image of the brain based on the parameters of the plane provided by the MSP calculation block and the 3D scout image provided by the 3D scout image providing block; a landmark detection block configured to receive the MSP image of the brain provided by the MSP image reconstruction block, detect at least two landmarks of a predetermined type, and provide coordinates of the at least two landmarks; a longitudinal reference line formation block configured to compute a longitudinal reference line based on the coordinates of the at least two landmarks provided by the landmark detection block, and provide parameters of the longitudinal reference line; and a view planning output interface block configured to transfer to a control system of a medical scanner the parameters of the plane provided by the MSP calculation block and the parameters of the longitudinal reference line provided by the longitudinal reference line formation block.

According to an aspect of another exemplary embodiment, provided is a system for detecting a trace of a longitudinal fissure of a brain and creating a corresponding reference line in at least one of axial and coronal brain sections, the system including: a binary mask formation block configured to receive a two-dimensional (2D) image of a working section, and compute a continuous binary mask defined by an image of the brain in the working section, and provide an image of the binary mask; a main axis determination block configured to receive the image of the binary mask provided by the binary mask formation block, compute main axes of the binary mask, and transfer parameters of the main axes; a working area determination block configured to analyze the parameters of the main axes provided by the main axis determination block, determine a working area for detecting a trace of a longitudinal fissure of the brain by a detector in the working section, determine a range of at least one from among horizontal movement and an angle of rotation of the detector at a test position, and provide the determined working area and the determined range; a longitudinal fissure trace detection block configured to receive the determined working area and the determined range from the working area determination block, detect the longitudinal fissure of the brain in the working section corresponding to parameters of the working area, compute a predetermined range of positions of the detector, test the detector at a plurality of possible positions in the computed predefined range, calculate a criterion based on pixels included in the detector at each of the tested plurality of possible positions, compare values of the criterion for the tested plurality of positions of the detector, detect a desired position based on a result of the comparison, and provide geometrical parameters for the detected desired position of the detector; and a reference line calculation block configured to receive geometrical parameters of the optimum position of the detector provided by the longitudinal fissure trace detection block, and compute the reference line based on a central axis of the detector located at the desired position in the working section.

According to an aspect of still another exemplary embodiment, provided is a non-transitory computer-readable storage medium storing a program for executing the above method by a computer.

BRIEF DESCRIPTION OF THE DRAWINGS

The above and/or other aspects will become apparent and more readily appreciated from the following description of certain exemplary embodiments, taken in conjunction with the accompanying drawings in which:

FIGS. 19A, 19B and 19C illustrate use of a generalized vector with directions during post-processing for detection of statistically invalid directions according to an exemplary embodiment;

FIG. 20 illustrates computation of an MSP as a regression plane constructed on a redundant set of points that are generated on each reference line according to an exemplary embodiment;

DETAILED DESCRIPTION

Figure 1:
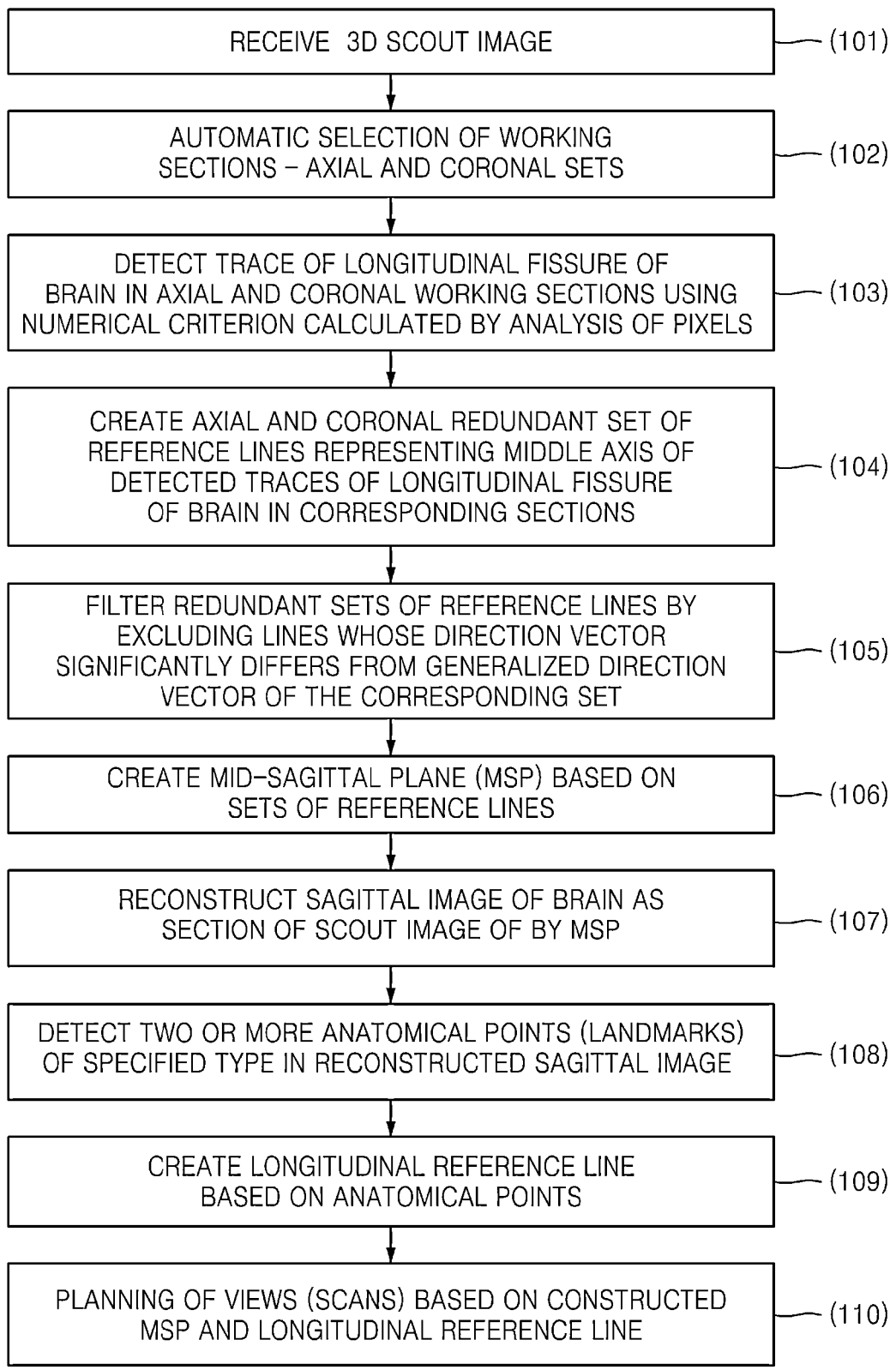
FIG. 1 is a flowchart of a method of automatically planning views in 3D images of a brain according to an exemplary embodiment.

Reference will now be made in detail to certain exemplary embodiments, which are illustrated in the accompanying drawings, wherein like reference numerals refer to like elements throughout. Exemplary embodiments may have different forms and should not be construed as being limited to the descriptions set forth herein. Accordingly, exemplary embodiments are merely described below, by referring to the figures, to explain aspects of the disclosure.

Exemplary embodiments described herein relate to medical images, in particular, to MRT of a brain. A three-dimensional image includes spatial pixels called voxels. Each voxel determines intensity of an image signal in a corresponding point of a space.

FIG. 1 is a flowchart of a method of automatically planning views in 3D images of a brain according to an exemplary embodiment. In the method, a preliminary image called a scout image is received (101).

In one embodiment, a 3D scout image is received as input data from medical equipment. In a specific case, a resolution of the scout image may be lowered to reduce acquisition time thereof.

Next, working sections are selected from two groups provided in axial and coronal sections. The working sections may be selected in consideration of geometrical and anatomical properties of an examined brain (102).

Selected sagittal and coronal sections representing two-dimensional (2D) gray images are processed. As a result of processing, traces of a longitudinal cleft (or fissure) of a brain in a considered working section are detected in the sagittal and coronal sections (103). A method of detecting the traces will be described later in detail. The method may use a numerical criterion based on analysis of intensities of pixels.

Reference lines are created in sections. Central axes of the detected traces of a longitudinal fissure of a brain in sections may be selected as the reference lines. Thus, the reference lines are grouped into two sets, i.e., axial and coronal sections. The two sets of the reference lines are redundant because the total number of lines exceeds a minimum number (i.e., two) needed for calculating a mid-sagittal plane (MSP) (104).

Since the sets of reference lines are redundant, a filtration of these sets is performed to remove lines whose direction vector essentially differs from a generalized vector having a direction of the corresponding set of reference lines (105).

An MSP is created based on the sets of reference lines. An operation of creating the MSP may be implemented by several methods, which will be described in detail later. For example, the MSP may be constructed as a regression plane on a set of points reconstructed on each of reference lines. Another approach uses generalization of directions of reference lines and formation of two vectors based on which the MSP is constructed (106).

A 2D image is reconstructed in a section of a 3D scout image defined by a specified plane based on the constructed MSP. Pixels from the 3D scout image, which are located closer to a section of the MSP may be used for the reconstruction (107).

An image reconstructed in the MSP is used to determine corresponding landmarks for obtaining a longitudinal reference axis in the image (108). Any acceptable landmarks and any method of searching for the landmarks may be used. The landmarks may be anatomical points located in the MSP.

A longitudinal reference line is computed based on the landmarks (109).

Detected parameters for the MSP and a longitudinal reference line are transmitted to a device for planning views. Specified parameters represent a full set of information for planning views (110).

Processing of an image with lower resolution is possible according to an exemplary embodiment, which is advantageous since it is a complicated task to recognize anatomical structures in a "degraded" image. It is also important to process an image with lower resolution because the resolution of a scout image is controlled to be lower to reduce the time required to acquire the image. Thus, a method according to an exemplary embodiment may improve reliability (or robustness) of automatically planning views.

Figure 2:
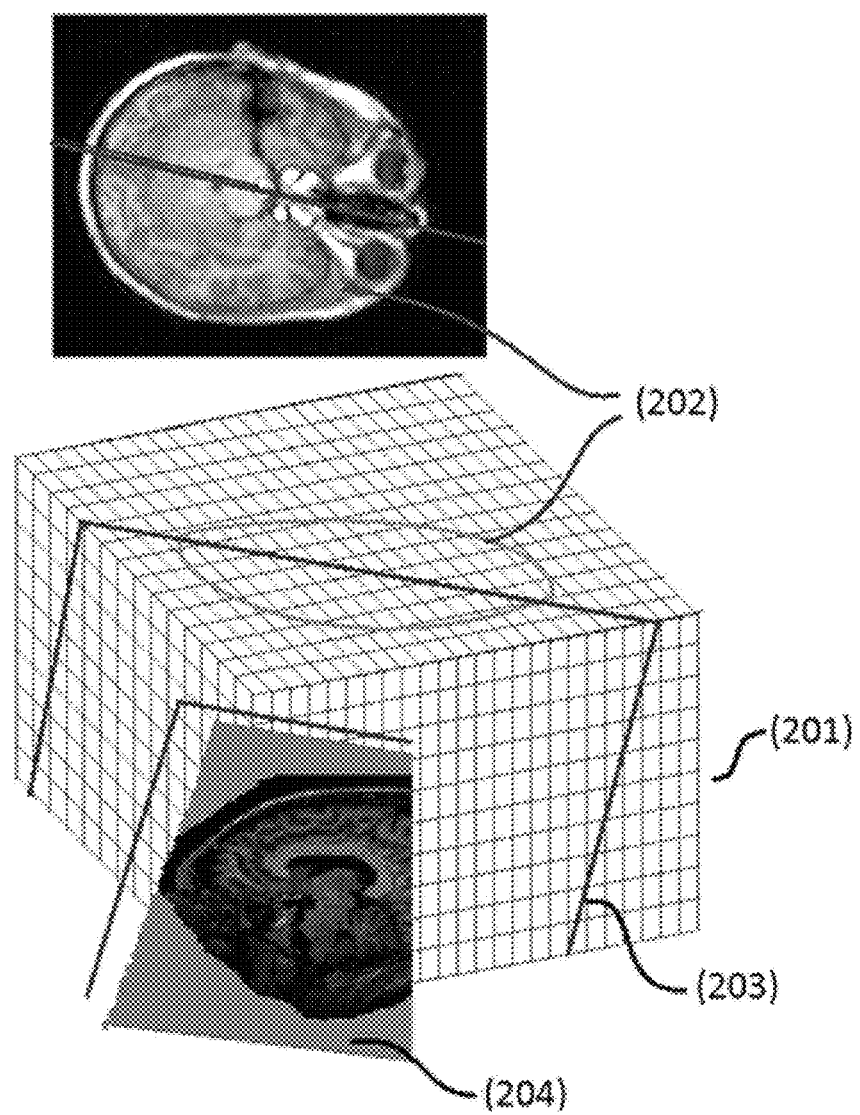
FIG. 2 illustrates an example of a brain orientation in a 3D scout image.

FIG. 2 illustrates definition of a process of planning of views and random orientation of a 3D scout image. Referring to FIG. 2, a cube 201 defines a 3D image, and an axial section 202 shows that brain orientation is irregular. A plane 203 of symmetry of a brain is oriented in an image volume so that its trace in a section does not coincide with a direction of a corresponding coordinate axis of the 3D scout image. Reference 204 shows an estimated mid-sagittal section of the brain obtained along the plane 203 of symmetry. To obtain diagnostic views in respective initial orientations, corresponding reference lines and planes need to be computed by using scout image processing.

Figure 3:
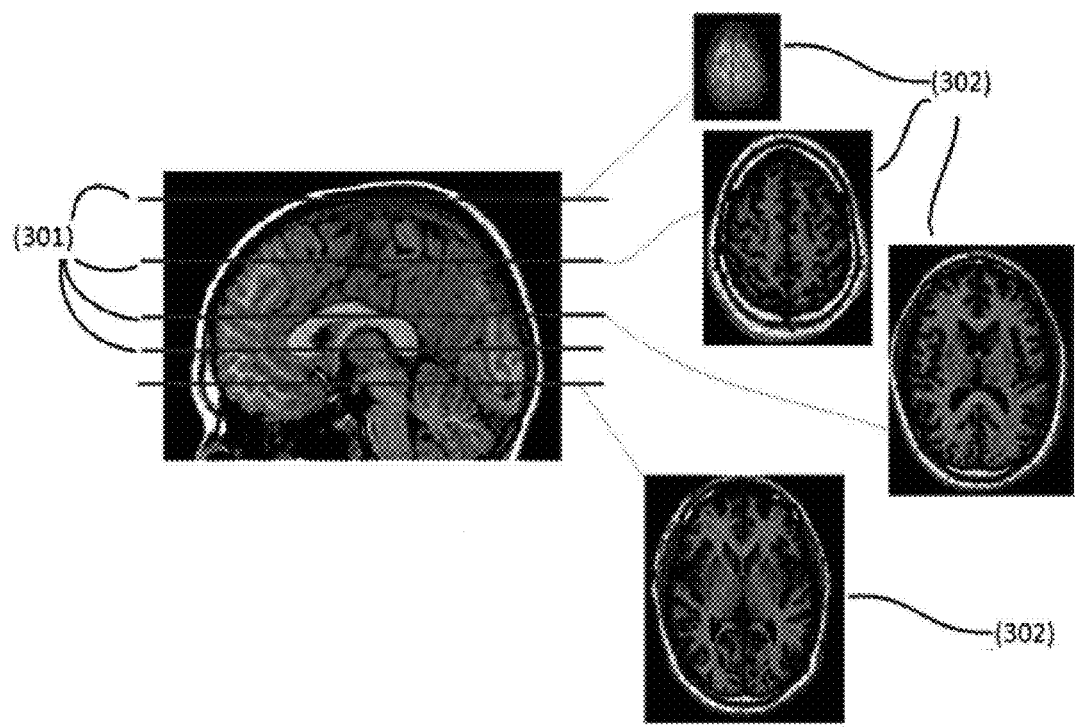
FIG. 3 illustrates an example of a trace of a longitudinal fissure of a brain in an axial section at various levels of height.

A scout image geometry is investigated by processing of sections which are provided in two-dimensional (2D) images. According to the method of FIG. 1, working sections are selected for subsequent processing (102). The working sections are selected both in axial and coronal planes. Such preliminary selection is performed because a trace from a section of the fissure that divides cerebral hemispheres is different for various sections and depends on locations of the sections. This feature is illustrated in FIG. 3 where references 301 and 302 denote levels of axial sections and images obtained in the axial sections, respectively. Further, not all sections may be suitable for obtaining of desired results. Thus, an approach for the preliminary analysis of an image of a brain and selection of appropriate working sections are proposed.

Figure 4A:
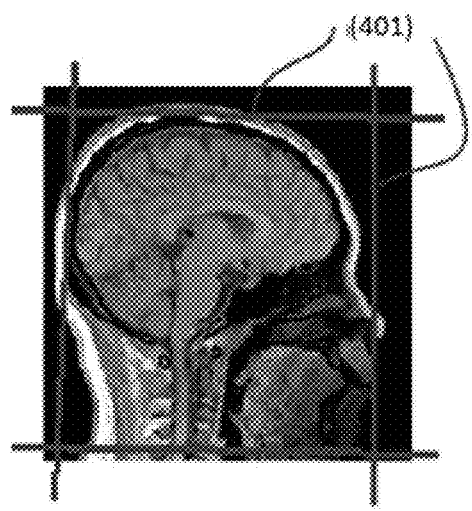
FIGS. 4A through 4C illustrate an example of selection of working axial sections.
Figure 4B:
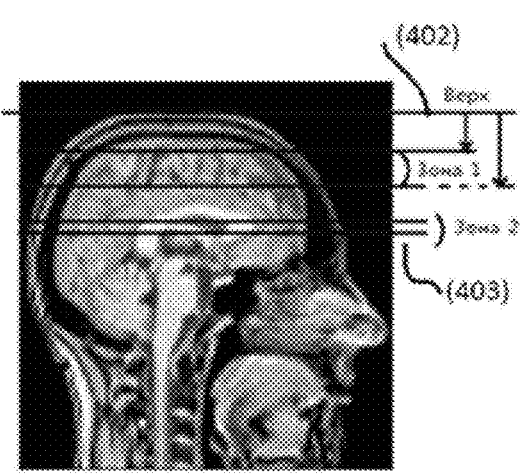
Figure 4C:
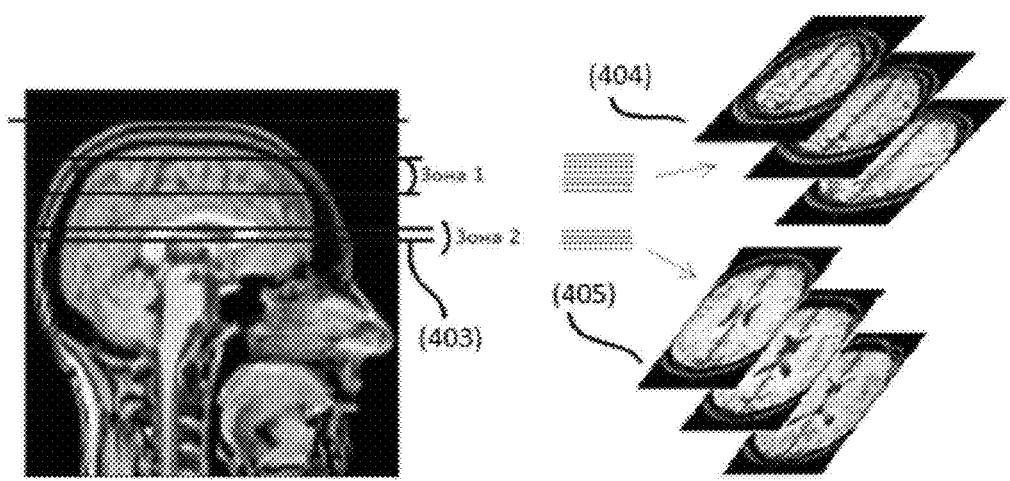

FIGS. 4A through 4C illustrates selection of axial working sections. Referring to FIGS. 4A through 4C, a rectangular parallelepiped (or bounding box) 401 is described as a volume around a head image. FIG. 4A shows an example of the parallelepiped 401 in a sagittal section taken in a middle portion of a scout image.

Coordinates of a top level 402 in an image of a head is determined, and levels 403 of sections are determined using a mean of predefined distances from the top level 402, and working zones for selection of the sections are determined based on the levels 403 of sections. Distances for the levels 403 may be determined in advance based on the statistical analysis of learning samples of images. FIGS. 4B and 4C illustrate the levels of the sections and the working zones. Sets 404 and 405 of axial sections having a certain fixed step therebetween by a vertical coordinate may be selected in each of the working zones, as illustrated in FIG. 4C.

Figure 5:
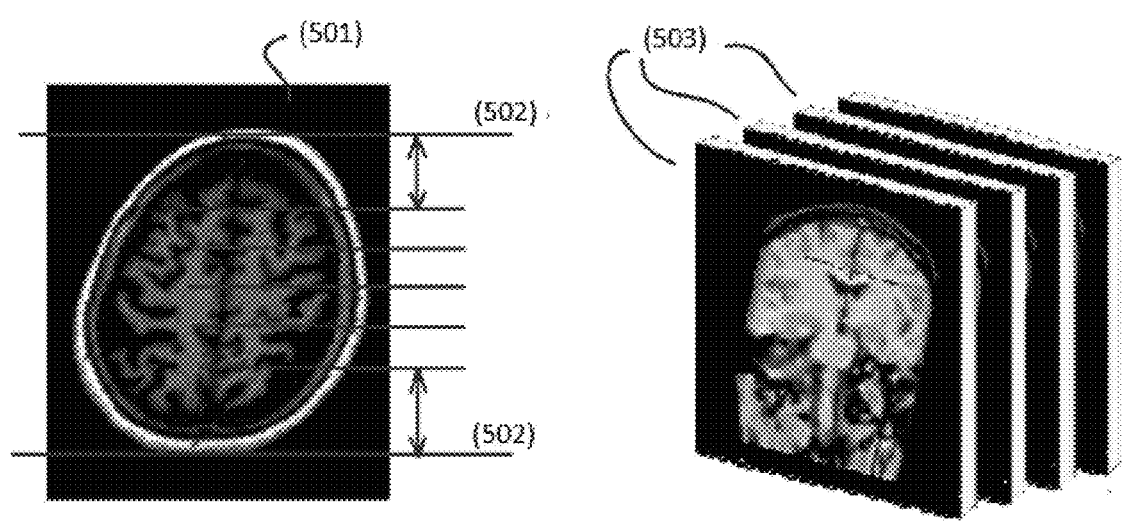
FIG. 5 illustrates an example of selection of working coronal sections.

FIG. 5 illustrates selection of working coronal sections. Referring to FIG. 5, a section 501 (e.g., an average section) is selected from among previously selected axial sections. A working zone 502 is determined in the selected section 501, and a set 503 of coronal working sections are obtained in the selected section 501 with a fixed step therebetween on a longitudinal axis.

Locations of the working zones, distances and geometrical proportions for selection of sections may depend on anatomy of a brain and properties of a scout image (e.g., sizes, position and relative size of an investigated head in a scout-volume). These parameters may be determined by a preliminary statistical analysis of a learning group of scout images.

Thus, an operation of obtaining two sets of working sections (i.e., axial and coronal sections) may be performed as described above.

Lines, i.e., traces of a section of a longitudinal fissure of the brain are detected in the selected working sections (103 in FIG. 1). An enhanced detection process that performs an analysis of an image in a section may be performed as described below.

Figure 6:
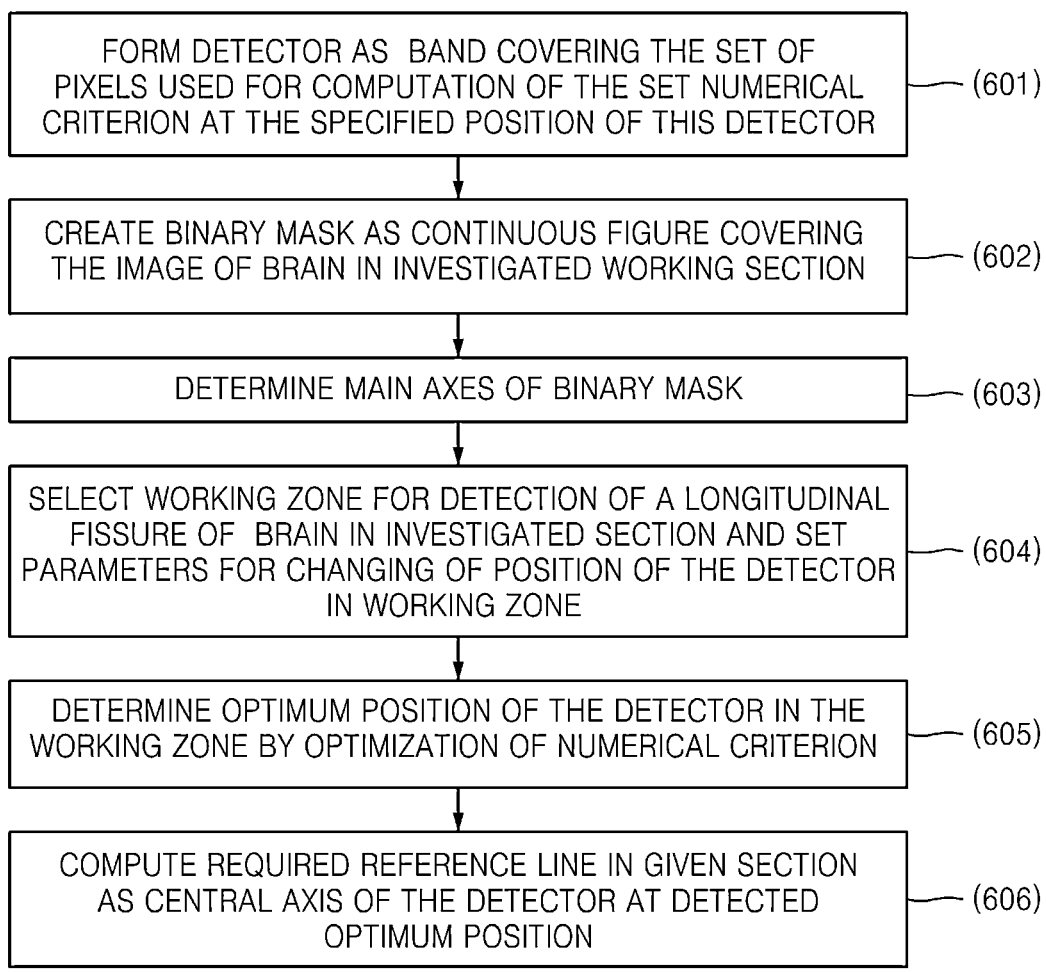
FIG. 6 is a flowchart of a process of detecting a longitudinal fissure of a brain in a section according to an exemplary embodiment.

FIG. 6 is a flowchart of a process of detecting a trace of a longitudinal fissure of the brain in a selected section according to an exemplary embodiment.

Referring to FIG. 6, a detector is formed as a band that covers a set of pixels and is used for computation of a numerical criterion at a specified position of the detector (601).

A continuous binary mask is created which is a plane figure covering an area of the brain in a working section of the image (602).

Main axes of the binary mask are calculated as axes of inertia of a plane FIG. 603).

A working zone, which is located in a geometrical structure of a binary mask, is selected for detection of a longitudinal fissure of the brain in an investigated section, and parameters, i.e., ranges of change of coordinates of a center and an angle of rotation of the working zone, are adjusted for a change in a position of the detector in the working zone (604). Here, the term "detector" refers to a part detected as a working zone.

A search is performed to determine an appropriate (e.g., optimum) position of the detector in the predefined working zone by using optimization of a numerical criterion (605).

A reference line required in a given section as a central axis of the detector at the determined optimum position thereof is computed (606).

Figure 7A:
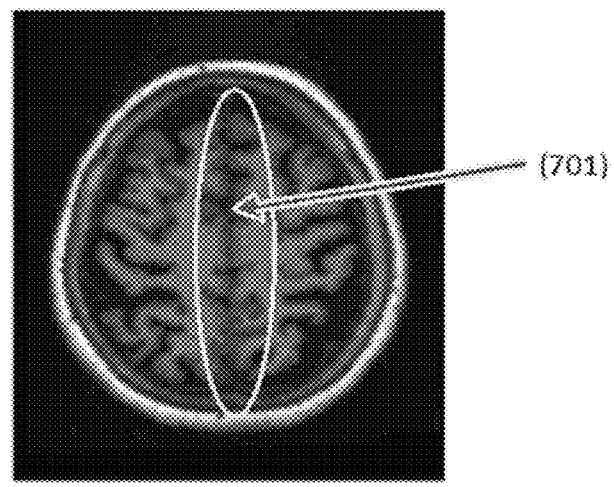
FIGS. 7A and 7B illustrate an example of a trace of a longitudinal fissure of a brain in sections wherein pixels in a fissure are darker than surrounding pixels belonging to white substance of the brain.
Figure 7B:
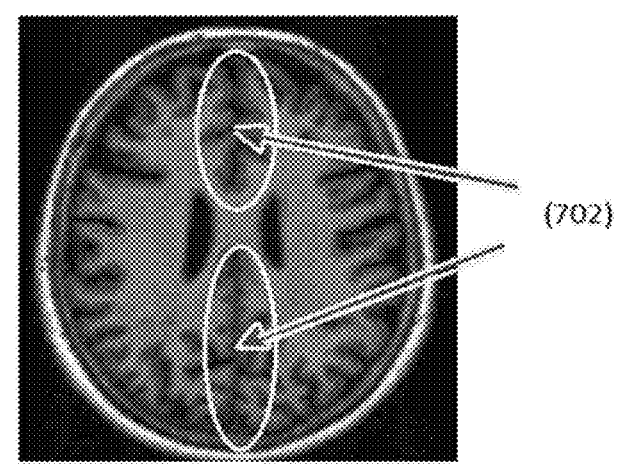

In detail, detection of a line of dividing cerebral hemispheres (or fissure) in an investigated section includes searching for a longest-distance line (e.g., continuous or dashed line) with set brightness properties. In an exemplary embodiment, the longest-distance line may be darker against the background of a white substance of the brain surrounding the line. Appearances of the longest-distance line may vary according to other protocols (or modes) of obtaining of an image. For example, in some protocols, the longest-distance line may appear lighter or may be provided with pixels having a specified brightness range. A method of detection of the longest-distance line may be changed according to brightness properties of the detected line. FIGS. 7A and 7B illustrate an example of detection of a trace of a longitudinal fissure of a brain in some sections. Referring to FIGS. 7A and 7B, a line in a first section shows a continuous structure 701 while in a second section a dashed line 702 is shown.

Figure 8:
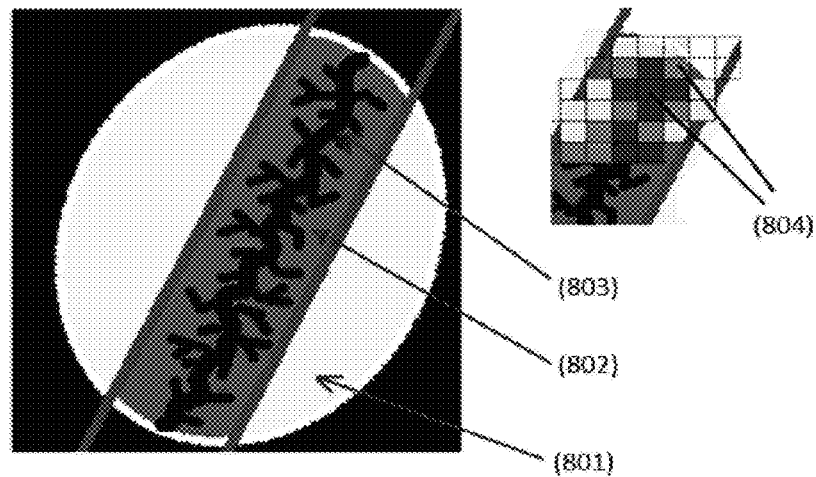
FIG. 8. Illustrates a detector for detecting a longitudinal fissure of a brain which is presented in a form of a band that limits an analysis of pixels and in which a stipulated quantitative criterion is computed according to an exemplary embodiment.

The method of determining a detector may be based on quantitative detection of a trace of a longitudinal fissure of a brain in some section. A detector is determined as a band covering a set of pixels and with capability of analysis of intensities and by computing a numerical criterion for estimating a possibility of the presence of a required line in the investigated zone. In particular, in one embodiment, normalized estimation of blackout of a site serves as a criterion for determining whether the required line is darker. Normalization is understood as division of corresponding brightness statistics in a zone, covered with the detector, by the total number of pixels in this zone. A concept of the detection is illustrated in FIG. 8. For a section 801 of the brain, a detector is formed as a band 802, and a required line (or fissure) in this example is shown as a curved dark structure 803. Intensities 804 of pixels are used to compute a criterion for blackout of a site.

Figure 9:
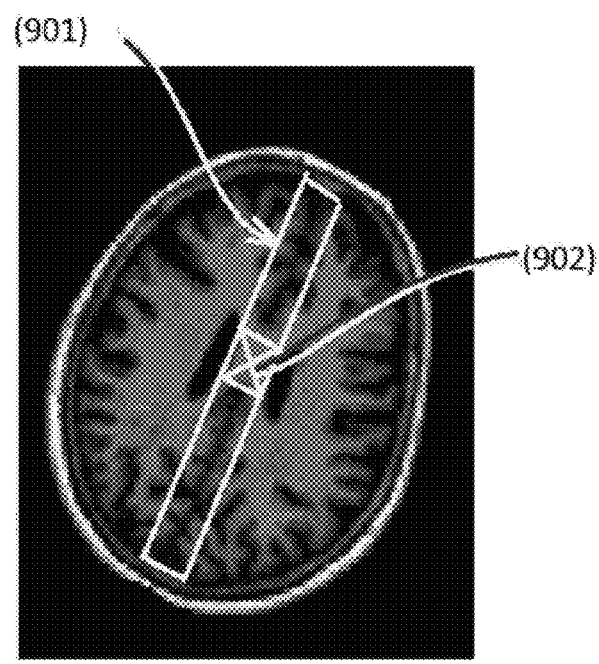
FIG. 9 illustrates a discontinuous form of a detector for detecting a longitudinal fissure of a brain according to anatomical features of the brain shown in an investigated section according to an exemplary embodiment.

During research of a plane section of an image, the detector may provide linear displacement and rotation thereof. A length of the detector is adaptively adjusted according to borders of a working zone. The detector may be discontinuous (i.e., have gaps) when required according to restrictions imposed by anatomical structures. For example, when a detected line in a specified section is discontinuous, the corresponding part of a band of the detector is excluded from computations. FIG. 9 shows a surrounding region 901 and a central region 902 of a band of a detector, wherein the central region 902 is excluded from computations. Such adaptive behavior of the detector may be predefined according to anatomical features of images in sections and learned in advance, and these properties may depend on position of the selected section.

Figure 10:
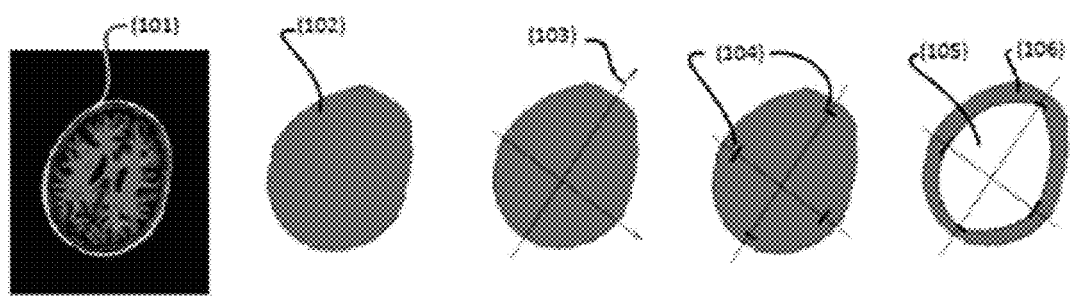
FIG. 10 illustrates creation of a binary mask in a section and computation of main axes of a binary mask according to an exemplary embodiment.

For determination of a working area, a binary mask is created in a section. The binary mask is provided as a continuous plane figure which covers a brain image in a section. In one embodiment, a largest continuous and lighter object (or area) on a darker background may be detected for mask construction. Operations of filling and selecting continuous objects in an image are used for search of a mask. In FIG. 10, references 101 and 102 denote a brain section in a gray image and a continuous binary mask, respectively. Such approach based on a largest covering of an object by a plane figure may be more reliable than construction of an ellipse according to a selected perimeter of the object. Main axes 103 of the mask 102 are built as an axis of inertia of a plane figure and the main axes 103 are used for determination of a working zone in a section by exclusion of external fields 104 whose relative size is predefined based on a preliminary statistical analysis of learning samples of images. References 106 and 105 denote the excluded fields and a working zone, respectively.

Figure 11:
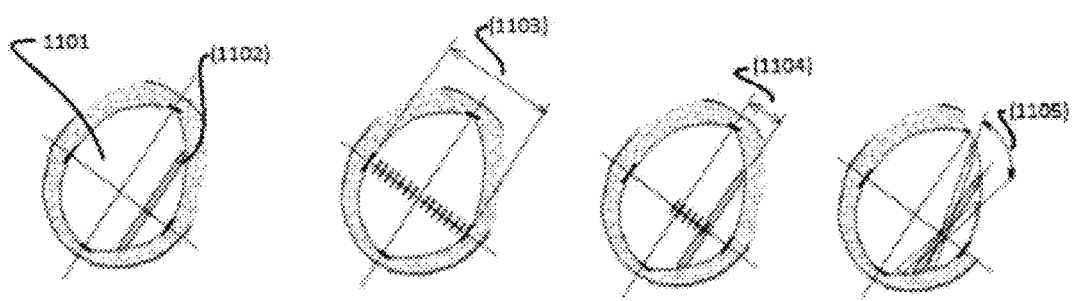
FIG. 11 illustrates estimation of ranges of change of parameters of a detector during examination of a predefined working area according to an exemplary embodiment.

The detector is applied to the working zone 105. A width of the detector is selected according to anatomical features in an image. The width needs to be slightly greater than an expected width of a detected line. A parameter for the width is selected based on preliminary statistical processing of images obtained from a fixed protocol (or mode of scanning equipment). A length of the detector adaptively changes depending on a position of the detector in the working zone 105. Since the detector needs to be checked in all acceptable positions in the working zone 105, ranges of change in parameters of position, e.g., linear displacement and rotation, and steps of changing the parameters are set. FIG. 11 illustrates examples of possible positions of a detector 1102 for setting linear displacement and angles of rotation. The detector 1102 is located at a random position in a working zone 1101. The range of linear displacement of the detector 1102 is designated as indicated by reference 1103. Also, a position of the detector 1102 in a linear displaced position is shown as having a range indicated by reference 1104. The range of variations of angle and position of the detector 1102 is shown as reference 1105.

A value of a numerical criterion is computed through an analysis of intensity of pixels corresponding to the detector for each checked position of the detector 1102. In one embodiment, the numerical criterion is computed through normalized estimation of blackout of a site. A method of computing the numerical criterion may be further explained later. Thus, a process for searching a desired (or optimum) position of the detector 1102 is performed. In one embodiment, is the desired position is determined as a position for which the numerical criterion of, e.g., blackout has a maximum value. The detected optimum position of the detector 1102 (or a central axis of the detector 1102) is used as the required line dividing cerebral hemispheres in a given section. In an initial stage, optimization may be implemented as an extensive search of all possible positions of the detector 1102 with a criterion check.

In one embodiment, several types of numerical criteria may be used for the detector 1102. For example, the numerical criteria may include at least one from among a criterion computed as a relative part of pixels among pixels corresponding to the detector with intensity lower than a set threshold value; a criterion computed as normalized weighted sum of intensities of pixels, and a criterion computed as normalized weighted sum of intensities of pixels when assuming that pixels have intensities satisfying a set range.

Figure 12:
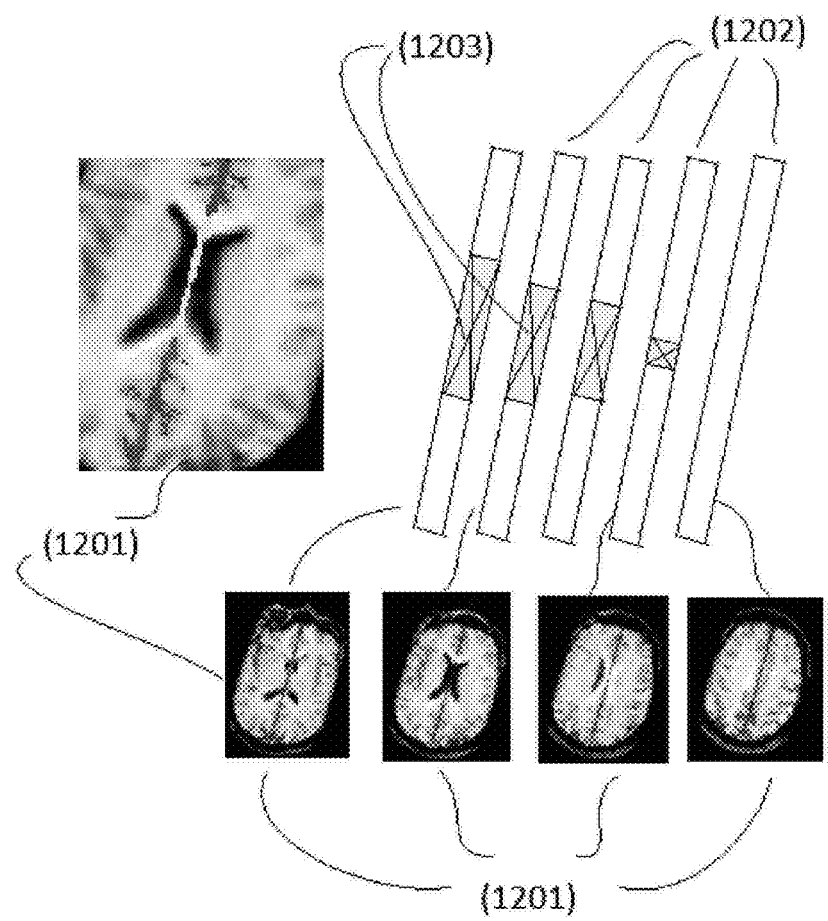
FIG. 12 illustrates a detector for detecting a longitudinal fissure of a brain with an interrupted form, a central part of which is excluded, sizes of the excluded part depending on properties of an examined section according to an exemplary embodiment.

Criteria for a detector with a more complex form than a continuous rectangular band may be used according to an embodiment. For example, detectors having a discontinuous form (i.e., with gaps) as shown in FIG. 9 may be used. FIG. 12 shows more detailed illustration. Examples of axial sections of a brain are designated by labels 1201, 1202, which are perimeters of corresponding detectors, 1203 which is a subarea excluded from computations of the criteria for a detector. In the above illustrative examples, a central part is excluded from the detector, and a size of an excluded part varies between different sections. The size of an excluded part depends on properties of a section. In the given examples, the excluded part is larger for bottom sections and smaller for top sections. Such regularity of construction of detectors corresponds to anatomic features of a brain in these sections. That is, in the bottom sections, a required line of dividing hemispheres is discontinuous around a center portion thereof, and in the top sections, a gap in the required line gradually decreases. An interrelation between the geometry of a subarea, excluded from the detector, and a height of a section, may be determined by the preliminary statistical analysis on learning samples of images.

Next, the above-described detection process is performed for all selected axial sections. A central axis of the detector, which is located at the detected optimum position in an investigated section, is determined as a line dividing cerebral hemispheres. The lines dividing cerebral hemispheres are grouped for their subsequent use for creation of an MSP. When the detection process fails in any section, this may not significantly affect construction of the MSP since robustness of a result is achieved by a redundant set of sections.

Figure 13:
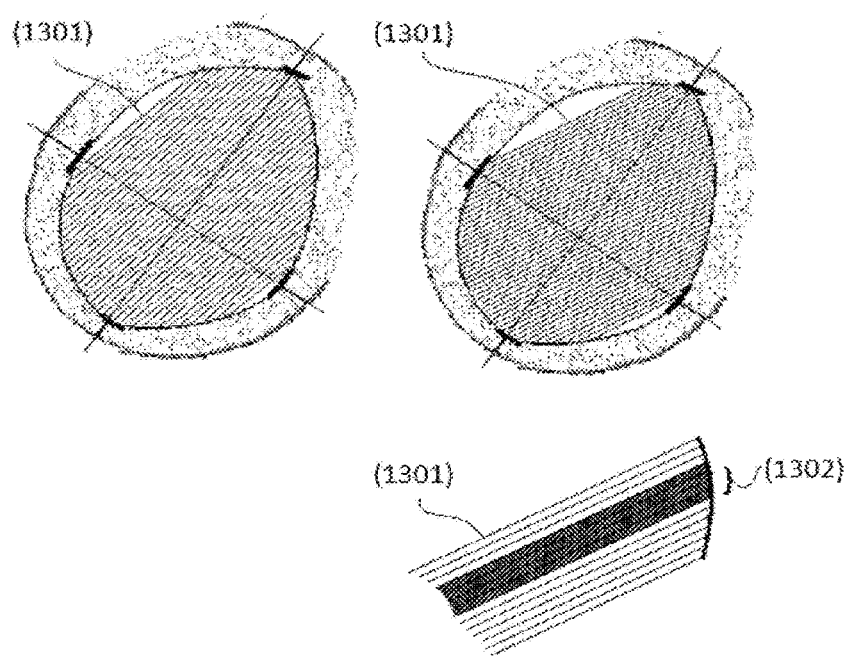
FIG. 13 illustrates a parallel detector for detecting a longitudinal fissure of the brain, which represents a bundle of parallel directed secants, according to an exemplary embodiment.

A process of detecting reference lines, which are constructed by optimization of criterion through search of all possible positions of the detector in each position, as illustrated in FIG. 11, may be time consuming. Therefore, a faster detection algorithm according to another exemplary embodiment called parallel detection is proposed. In the algorithm, the detector is built as a bundle of several parallel secants as shown in FIG. 13. Referring to FIG. 13, a set of collinear lines 1301 is provided for each checked angle of orientation of the detector. These lines may be called secants as the lines cross all pixels in a working zone. Statistics of intensities of pixels crossed by lines, which is used in computation of criterion of detection of a fissure, are collected along each line. A distance between parallel secants is selected to be smaller than a width of the applied detector, therefore the detector may be considered as a bundle 1302 of parallel secants that are collected from the set of collinear lines 1301. A criterion for the detector is computed along each secant as a combination of the corresponding statistics of several secants collected in the bundle, based on statistics of intensities of pixels. Thus, a process of parallel detection is performed. In detail, the process of parallel detection is performed as follows.

A working zone is selected in an investigated section, and ranges of displacements and rotation of the detector are selected in the selected working zone. A width of the detector is selected and a distance between secants is set.

An optimization process for the criterion, tested through a predefined range of angles, is performed. Specifically, the following procedures are performed for each tested angle.

A set of parallel secants is built within the working zone, wherein the set of parallel secants are directed according to a tested angle of rotation of the detector. Required statistics of intensities of pixels are computed for each secant.

The detector is reconstructed as a bundle of secants for all possible bundles in a set of lines. Search for all possible bundles corresponds to linear displacement of the detector from one line to another. A value of criterion is computed for each linear position of the detector. As a result, an optimum value of the criterion is detected, corresponding to some optimum linear displacement of the detector at a fixed angle.

Optimum values of the criterion detected by the method described above for each tested angle in the predefined range are compared with each other to determine a global optimum value.

The global optimum value of the criterion and a position of the detector corresponding thereto are determined as a result. A central axis of the detector at the detected optimum position is determined as the required reference line that divides cerebral hemispheres in a processed section.

The detection, executed by the method described above according to an exemplary embodiment, may be faster than directly searching all positions of the detector since the above method effectively uses once computed brightness statistics of pixels for each secant and does not demand the repeated analysis of pixels for each new linear displacement of the detector. Furthermore, the repeated analysis of pixels is not required due to direct construction of a band of the detector and its crossing with borders of a working zone because such crossings are already executed upon construction of secants and are implicitly considered in collecting statistics of the pixels crossed by each secant.

Thus, a procedure of detecting lines of dividing cerebral hemispheres in axial sections may be performed as described above.

Detection of a line (or fissure) that divides the cerebral hemispheres in coronal sections may be performed similarly to the process for axial sections described above. A difference in construction of a working zone for detection may exist since the structures of images in coronal and axial sections differ from each other.

FIGS. 14A through 14F illustrate an example of construction of a working zone 1406 in a coronal section.

Figure 14A:
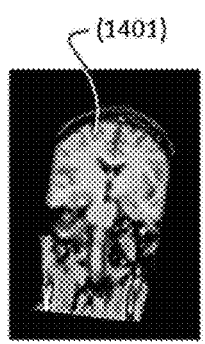
FIGS. 14A through 14F illustrate construction of a working area for a detector for detecting a longitudinal fissure of a brain in a coronal section according to an exemplary embodiment.

A coronal section 1401 is selected (FIG. 14A.1).

Figure 14B:
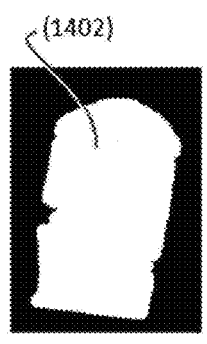

A continuous binary mask 1402 is provided to cover images of a brain in the coronal section 1401. In one embodiment, the binary mark 1402 is determined as a largest continuous light area in the coronal section 1401 (FIG. 14B).

Figure 14C:
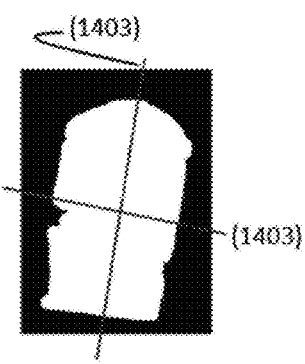

Main axes 1403 of the binary mask 1402 are computed as axes of inertia of a continuous plane figure (FIG. 14C).

Figure 14D:
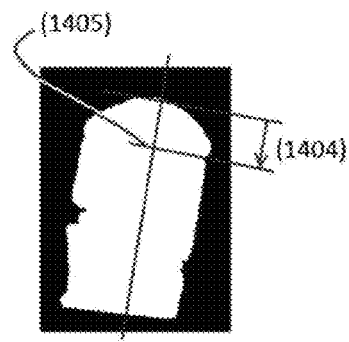
Figure 14E:
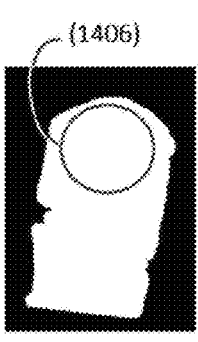

A center 1405 of the working zone is determined on a vertical axis, and a distance 1404 from a top border of the binary mask 1402 is selected based on preliminary executed statistical analysis of coronal sections in learning samples of images (FIG. 14D).

The working zone 1406 is selected in the form of a circle with a center determined by the method described above. A radius of this circle depends on the size of a head portion in an image, and a corresponding proportion may be determined preliminarily during the statistical analysis of learning samples of images. FIGS. 14A through 14F illustrate construction of the working zone 1406.

Figure 14F:
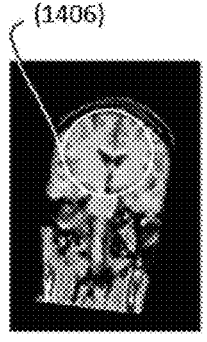

FIG. 14F shows localization of the constructed working zone 1406 on a gray image of the coronal section 1401.

Figure 15A:
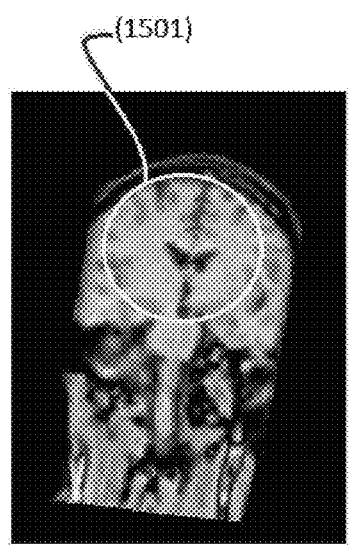
FIGS. 15A and 15B illustrate a detector for detecting a longitudinal fissure of a brain in a working zone of a coronal section according to an exemplary embodiment.
Figure 15B:
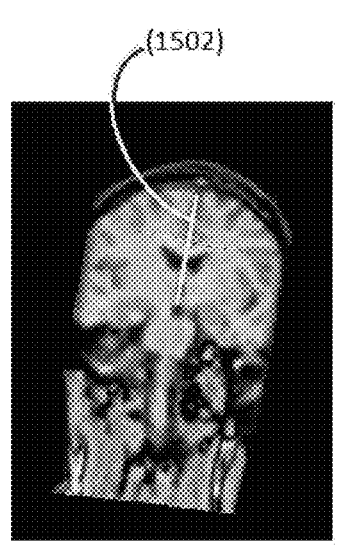

In a working zone in the coronal section determined by the method described above, a procedure of detecting a line which divides hemispheres may be performed similar to the procedure described above for axial sections. FIGS. 15A and 15B illustrate example results of detection in a coronal section. FIG. 15A shows a working zone 1501 of a detector at a detector at a detected optimum position. FIG. 15B shows a central axis of a detector at a detected optimum position.

Figure 16:
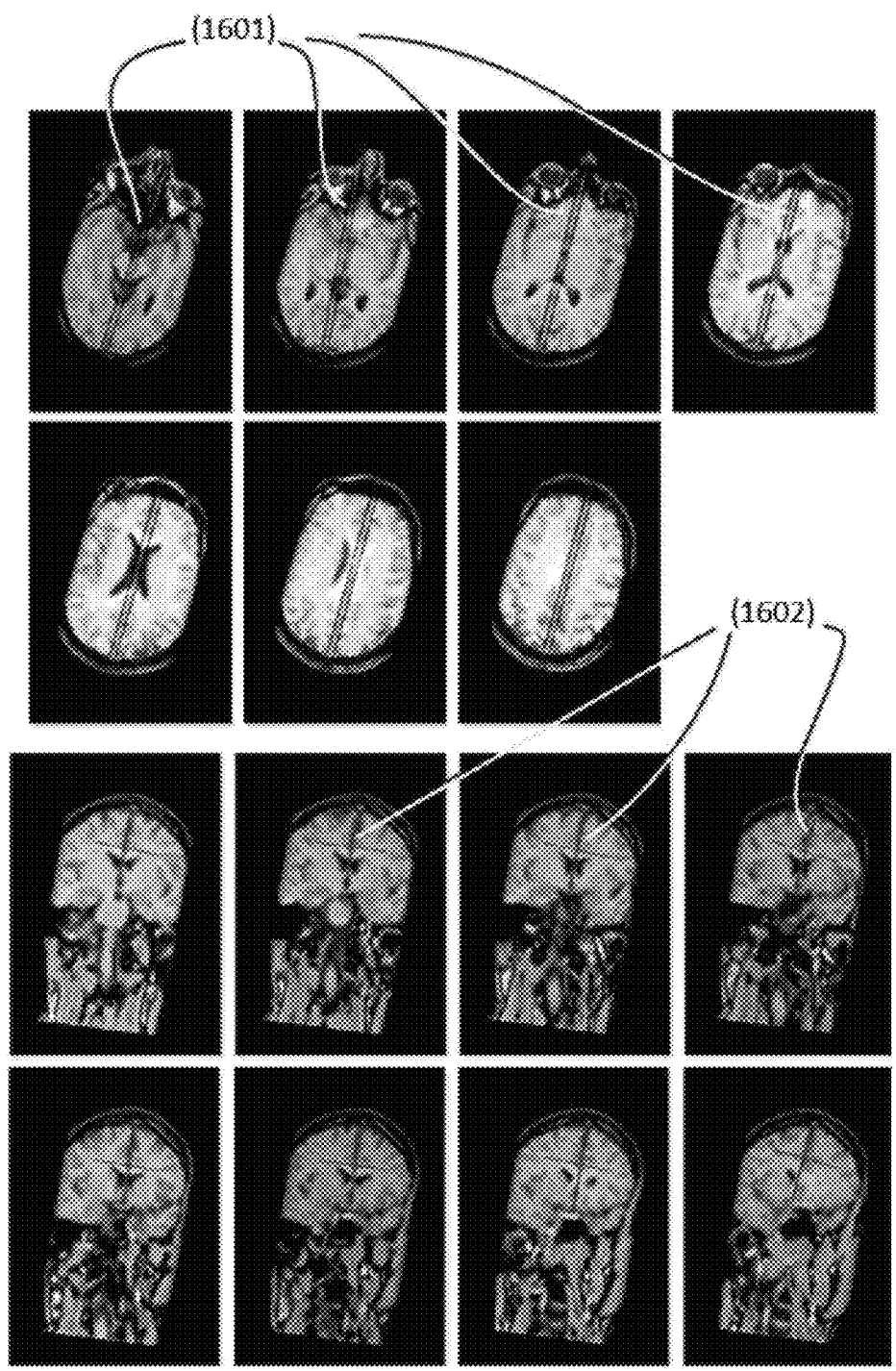
FIG. 16 illustrates detected positions of a longitudinal fissure of a brain in predefined sections according to an exemplary embodiment.

Corresponding reference lines may be determined after processing by a detector for detecting all axial and coronal sections. The references lines may be determined as central axes of detectors at the detected optimum positions. Here, it is assumed that the central axes of the detectors correspond to the central axes of sections of fissures, i.e. the central axes of lines of dividing of the cerebral hemispheres in considered sections. Reference lines are represented as a result in a 3D view. That is, a third coordinate is a corresponding coordinate of an investigated plane section (i.e. a corresponding coordinate of an investigated layer in a 3D scout image). FIG. 16 shows an example result of detection of lines of dividing hemispheres for selected sets of axial and coronal sections. Referring to FIG. 16, reference lines 1601 for axial sections and references lines 1602 for coronal sections are shown. The reference lines are used for subsequent construction of an MSP.

Figure 17A:
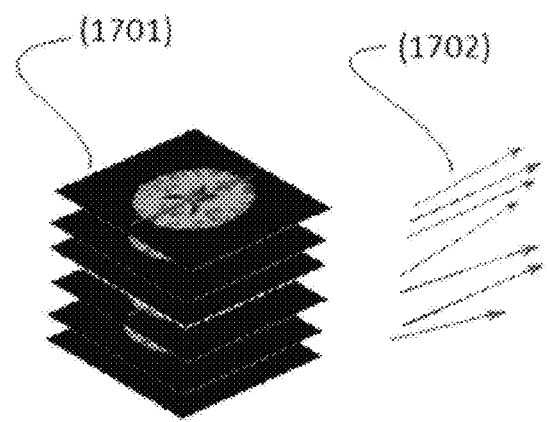
FIGS. 17A and 17B illustrate two sets of reference lines constructed for axial and coronal sections according to an exemplary embodiment.
Figure 17B:
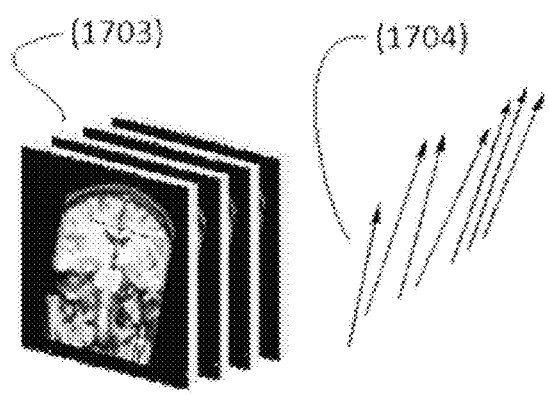

FIGS. 17A and 17B illustrate example results of processing of sections. FIG. 17A shows a set 1702 of axial reference lines created in axial sections 1701. FIG. 17B shows a set 1704 of coronal reference lines 1704 created in coronal sections 1703.

When no detection process detects a fissure, the corresponding sections are excluded from further analysis. In this case, the number of obtained reference lines decreases. However, a process of constructing an MSP is not terminated since sets of working sections and corresponding sets of reference lines are provided to be redundant. Moreover, by using redundant sets, a procedure of a filtration of results may be performed to substantially eliminate inaccurately determined reference lines.

Figure 18:
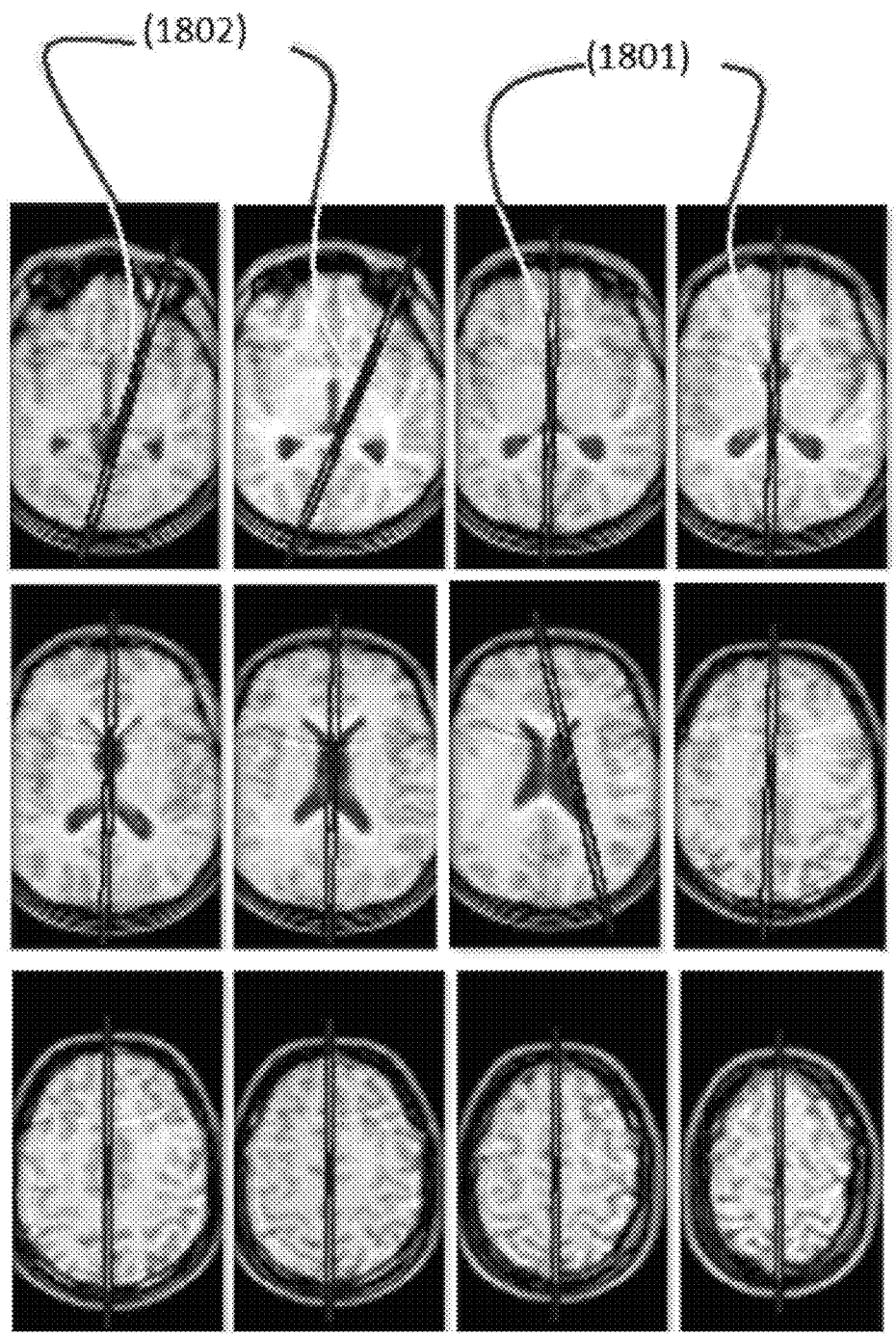
FIG. 18 illustrates unreliable lines of a longitudinal fissure of a brain in a set of axial sections according to an exemplary embodiment.

Since all the computed reference lines are not suitable for the subsequent construction of an MSP, some of results of the computation may be unreliable. FIG. 18 illustrates successfully detected reference lines 1801 and unreliable reference lines 1802. Referring to FIG. 18, three lines from twelve lines in axial sections may be considered unreliable in comparison with the remaining nine lines. This may be visually recognizable by using direction vectors of the computed reference lines. The filtration of the collected reference lines is performed to eliminate such unreliable results.

An example of the filtration process is illustrated in FIGS. 19A through 19C. FIG. 19A shows a set of lines including lines 1901 with a reliable directivity vector and lines 1902 with an unreliable directivity vector. FIG. 19B shows a generalized direction vector 1903 constructed for the whole set of reference lines. Determination of the generalized direction vector 1903 is based on use of deficiency which represents a normalized length of an orthogonal vector-remainder appearing at projection of one vector on another. Such orthogonal vector-remainder is a natural measure of noncollinearity of compared vectors. A vector, for which the sum of lengths of the orthogonal vector-remainders appearing at projection of the whole set of directions of reference lines thereon is minimum, is considered as generalized directivity vector. Thus, the constructed direction may be considered as collinear by the whole set of reference lines based on a minimum total deficiency and collected by the orthogonal vector-remainders from projecting of the lines on this vector. Here, it is assumed that all directivity vectors are normalized, i.e. deduced to a unit length, and the total deficiency is normalized by division on number of vectors.

The filtration of a set of reference lines may be performed further as follows. The directivity vector of each of lines is projected on the generalized directivity vector to compute deficiency, i.e., a length of the orthogonal vector-remainder which occurs upon projection. When a value of the deficiency exceeds a threshold, the direction of a tested reference line is considered significantly different from a direction of the generalized vector, and the tested reference line is excluded from the set (FIG. 19B. After such filtration, a reduced set of reference lines (FIG. 19C exists, and reliability of the whole solution is increased.

The filtration described above may be performed both for axial and for coronal sets of the detected reference lines.

An MSP of a brain is provided based on reference lines collected in sections. In one embodiment, three approaches to construction of an MSP may be used. That is, a first approach to construction of a regressive plane on a set of the points restored on segments of reference lines, a second approach to construction of an MSP by using two generalized directivity vectors constructed based on a set of axial reference lines, and a third approach to construction of an MSP by using two generalized directivity vectors constructed based on sets of axial and coronal reference lines may be used.

An exemplary embodiment of the first approach is illustrated in FIG. 20. Referring to FIG. 20, reference lines are designated as 2001 and points 2002 are generated on the reference lines. An MSP 2003 is constructed based on the points 2002. For example, the MSP 2003 may be constructed based on the points 2002 using a least square method.

Figure 21A:
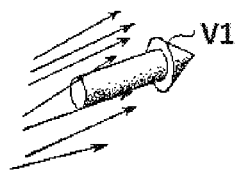
FIGS. 21A through 21F illustrates computation of an MSP based on two generalized direction vectors computed based in axial reference lines according to an exemplary embodiment.
Figure 21B:
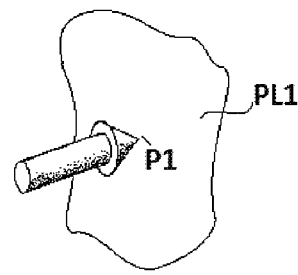
Figure 21C:
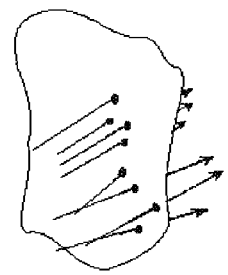
Figure 21D:
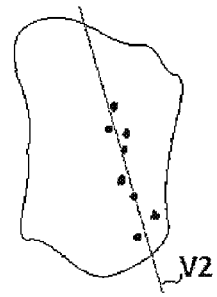
Figure 21E:
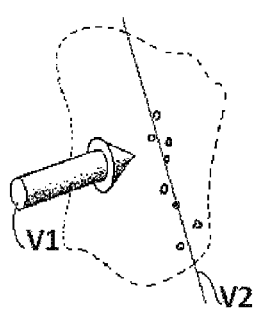
Figure 21F:
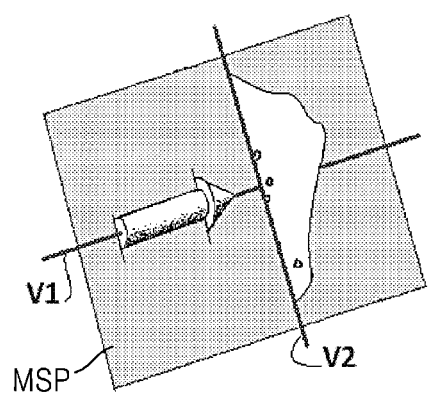

FIGS. 21A and 21F illustrate an exemplary embodiment of the second approach. Referring to FIGS. 21A through 21F, the second approach includes: computation of a vector V1 as the generalized direction of all axial reference lines (FIG. 21A) according to the above determination; computation of boundary points of all axial reference lines as points of intersection of specified lines with borders of binary masks in corresponding axial sections; computation of a central point P1 with coordinates determined as averaged coordinates of the boundary points; construction of a plane PL1 that is orthogonal to the vector V1 and passes through the central point P1 (FIG. 21B); determination of points of intersection of all reference lines from an axial set with the constructed plane PL1 and obtaining a set of the points of intersection (FIG. 21C); construction of a reference line V2 as a regression straight line passing through the set of the points of intersection (FIG. 21D); and construction of an MSP as a plane in which a normal vector is orthogonal to the vectors V1 and V2 and passing through the previously detected central point P1 (FIG. 21E and FIG. 21F).

The third approach is similar to the second one but with a difference in that correction of one of reference vectors is performed at a last stage. A vector V3 (not shown) which is obtained as a weighted sum of the vector V2 and a generalized vector V_COR (not shown) with a direction of coronal reference lines are used instead of the vector V2. A proportion of the weighted sum may be specified experimentally. In one embodiment, identical weight multipliers may be used for the specified vectors.

Thus, the MSP is provided based on obtained reference lines as described above.

A specified sagittal image, corresponding to a section of a scout-volume by the plane is reconstructed based on the constructed MSP. Pixels of the specified image may be determined as pixels of a volume closest to the MSP.

A pair or more of landmarks, of which type is stipulated in advance, is detected in the reconstructed sagittal image. Any method of detection of the landmarks may be used, and thus is not specifically described in exemplary embodiments. Also, the selection of landmarks is not specifically described. For example, points of the landmarks may be chosen according to Talairach's atlas. A reference straight line is further provided in a mid-sagittal section based on the detected landmarks. When there are two specified points, the straight reference line is provided to pass through these two points. A larger number of landmarks may be used if needed, and in this case, a reference straight line may be provided using the larger number of landmarks by using more complex methods.

The constructed MSP and a longitudinal reference straight line constructed by the detected landmarks in the MSP show a full set of information needed for planning of views (sections) of a brain, and the full set of information is output as parameters for the described method of planning of views.

Figure 22:
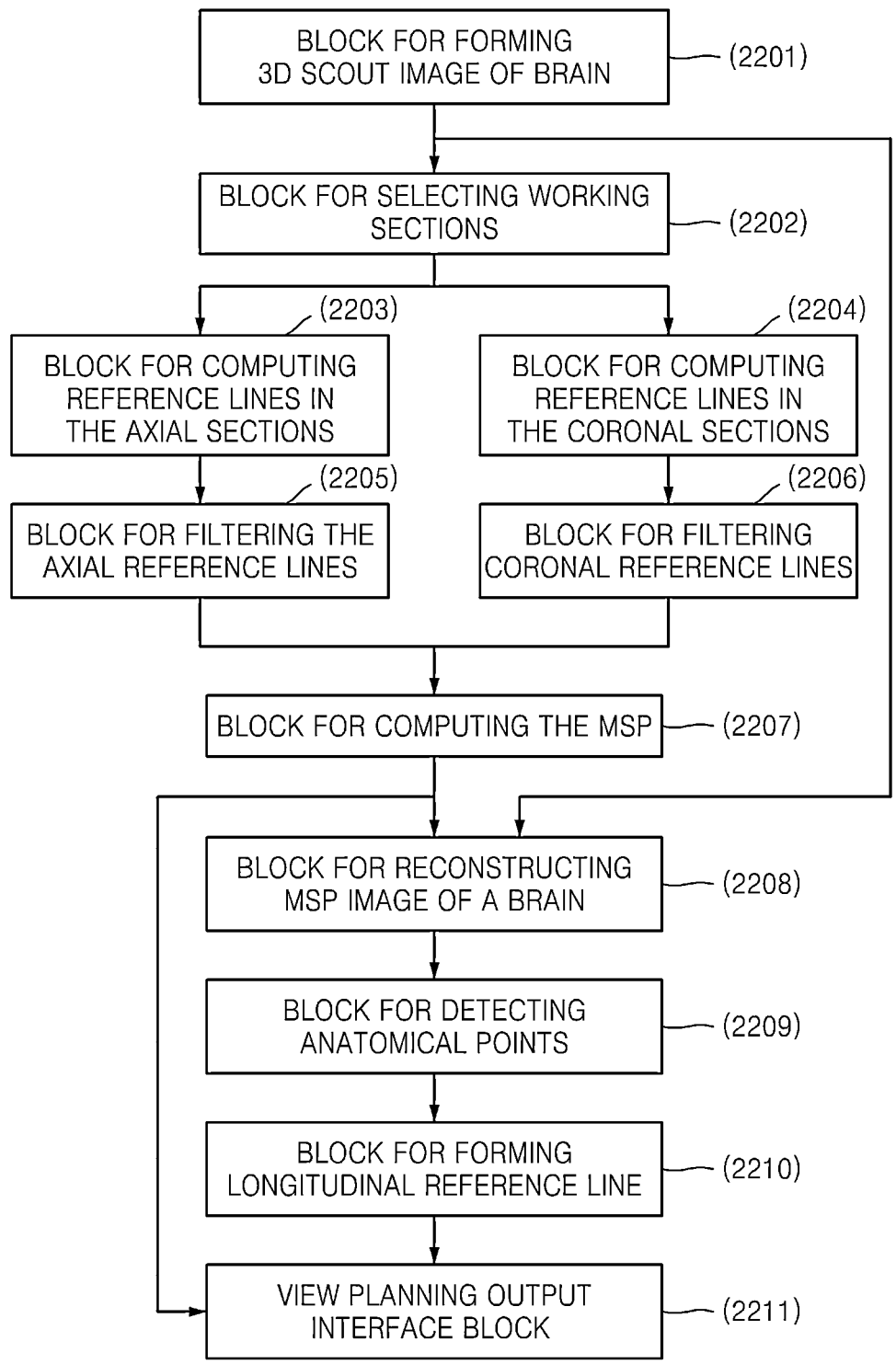
FIG. 22 illustrates a system of automatic planning of views in a 3D image of a brain according to an exemplary embodiment.

Exemplary embodiments may incorporate a common design to include a system for automatic planning of views (or scans) in a 3D image of a brain. A system according to an exemplary embodiment is configured to implement the method described above and compute the MSP and corresponding reference lines. Referring to FIG. 22, the system includes a 3D scout image formation block 2201, a working section selection block 2202, an axial section reference line calculation block 2203, a coronal section reference line calculation block 2204, an axial reference line filtration block 2205, a coronal reference line filtration block 2206, an MSP calculation block 2207, an MSP image reconstruction block 2208, a landmark detection block 2209, a longitudinal reference line formation block 2210, and a view planning output interface block 2211.

The 3D scout image formation block 2201 collects data of a medical image, creates a 3D scout image from the data of the medical image, and transmits the 3D scout image to the working section selection block 2202 and the MSP image reconstruction block 2208.

The working section selection block 2202 analyzes the 3D scout image, selects axial and coronal working sections, forms two corresponding sets from the selected axial and coronal working sections, and transmits the two sets to the axial section reference line calculation block 2203 and the coronal section reference line calculation block 2204.

The axial section reference line calculation block 2203 analyzes axial sections, detects traces of a longitudinal fissure of a brain in the axial sections, computes reference lines as central axial lines of the detected traces, and transmits the reference lines to the axial reference line filtration block 2205.

The coronal section reference line calculation block 2204 analyzes coronal sections, detects traces of a longitudinal fissure of a brain in the coronal sections, computes reference lines as central coronal lines of the detected traces, and transfers the reference lines to the coronal reference line filtration block 2206.

The axial reference line filtration block 2205 analyzes the obtained set of axial reference lines, excludes, from the set, lines whose directivity vector significantly differs from a generalized vector with a direction of the whole set of the axial reference lines, and transfers a reduced set of reference lines to the MSP calculation block 2207.

The coronal reference line filtration block 2206 analyzes the obtained set of coronal reference lines, excludes from the set, lines whose directivity vector significantly differs from a generalized vector with a direction of the whole set of the coronal reference lines, and transfers a reduced set of reference lines to the MSP calculation block 2207.

The MSP calculation block 2207 receives the filtered sets of axial and coronal reference lines, forms a plane based on the sets of axial and coronal reference lines, and transfers parameters of the plane to the MSP image reconstruction block 2208 and the view planning output interface block 2211.

The MSP image reconstruction block 2208 receives the parameters and the 3D scout image, forms an MSP image of the brain based on a section in the scout image of the MSP, and transfers the MSP image to the landmark detection block 2209.

The landmark detection block 2209 receives the MSP image of a brain, analyzes the MSP image, detects a pair or more of landmarks of a certain type, and transfers coordinates of the landmarks to the longitudinal reference line formation block 2210.

The longitudinal reference line formation block 2210 receives coordinates of the landmarks, computes a longitudinal reference line based on the landmarks, and transfers parameters of the longitudinal reference line to the view planning output interface block 2211.

The view planning output interface block 2211 receives the MSP and the longitudinal reference line and transfers parameters thereof to a control system of a medical scanner.

The above elements 2201 to 2211 may be implemented with at least one processor module. That is, the above elements 2201 to 2211 may be implemented as an array of a plurality of logic gates, or may be implemented as a combination of a general-use microprocessor and a memory that stores a program executable by the microprocessor. Also, the above elements 2201 to 2211 may be implemented as an application program module.

Figure 23:
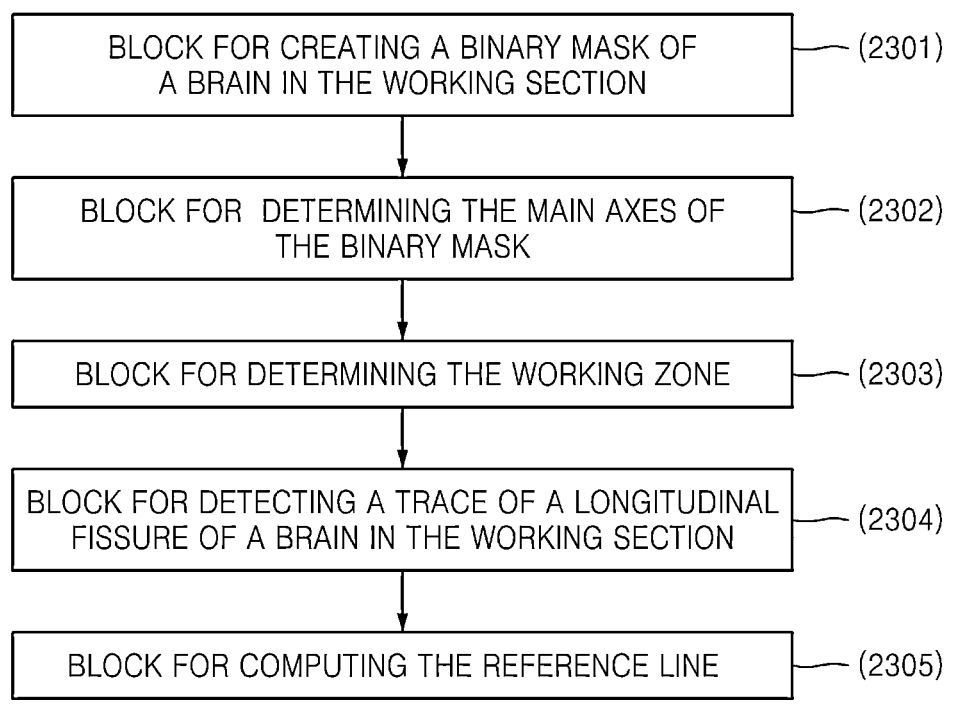
FIG. 23 illustrates a system for detecting a longitudinal fissure of the brain and constructing a reference line in a section according to an exemplary embodiment.

FIG. 23 illustrates a system for detecting a trace of a longitudinal fissure of a brain and creating a corresponding reference line in axial or coronal brain sections according to an exemplary embodiment. The system according to an exemplary embodiment may implement the above-described detection method. Referring to FIG. 23, the system includes a binary mask formation block 2301, a main axis determination block 2302, a working area determination block 2303, a longitudinal fissure trace detection block 2304, and a reference line calculation block 2305.

The binary mask formation block 2301 receives a gray 2D image of a working section, computes a continuous binary mask covering an image of a brain in the working section, and transfers an image of the binary mask to the main axis determination block 2302.

The main axis determination block 2302 receives the image of the binary mask, computes main axes of the binary mask, and transfers parameters of the main axes to the working area determination block 2303.

The working area determination block 2303 analyzes the binary mask and its main axes, determines a working area for detection of a trace of a longitudinal fissure of the brain by a detector in the working section, determines ranges of horizontal movement and an angle of rotation for a test position of the detector, and transfers the determined working area and ranges to the longitudinal fissure trace detection block 2304.

The longitudinal fissure trace detection block 2304 for detecting a longitudinal fissure of a brain in a working section receives the parameters of the working area, computes ranges of positioning of the detector, tests the detector at all possible positions in a predefined range, calculates a quantitative criterion by the analysis of pixels covered by the detector at each of its tested positions, compares the computed values of the criterion for all the tested positions of the detector, detects a position corresponding to an optimum value of the criterion, and transfers geometrical parameters for the detected optimum position of the detector to the reference line calculation block 2305.

The reference line calculation block 2305 receives geometrical parameters of the optimum position of the detector and computes a reference line as a middle axis of the detector located at the optimum position in a working section.

The above elements 2301 to 2305 may be implemented with at least one processor module. That is, the above elements 2301 to 2305 may be implemented as an array of a plurality of logic gates, or may be implemented as a combination of a general-use microprocessor and a memory that stores a program executable by the microprocessor. Also, the above elements 2301 to 2305 may be implemented as an application program module.

A method according to exemplary embodiments is applicable to planning of views in medical images based on the analysis of a preliminarily obtained draft 3D image such as a scout image, and in particular, images acquired by an MRT, an X-ray tomography, etc.

In a method according to exemplary embodiments, the total time required for obtaining diagnostic scans may be reduced due to automated planning of views, and thus, an overall process of obtaining images of the brain may have improved efficiency. Furthermore, automatic planning of views may obviate a need for medical personnel to perform the routine manual job needed for a procedure of obtaining images of the brain.

According to exemplary embodiments, robustness of a process may be increased. A method according to exemplary embodiments is applicable to scout images with both higher and lower resolutions, wherein low resolution may be used to reduce the time of acquisition of a scout image.

Methods according to exemplary embodiments may be written as computer programs and be implemented in general-use digital computers that execute the programs using a computer-readable recording medium. A data structure used in the above-described embodiments may be recorded in a computer-readable recording medium by using various methods. Examples of the computer-readable recording medium include magnetic storage media (e.g., read only memories (ROMs), random access memories (RAMs), universal serial buses (USBs), floppy disks, hard disks, etc.) and storage media such as optical recording media (e.g., compact disc-ROMs (CD-ROMs) or digital video disks (DVDs)) and personal computer (PC) interfaces (PCIs) (e.g., PCI, PCI-express, Wi-Fi, etc.).

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art

What is claimed is:

1. A method of automatic planning a view in a three-dimensional (3D) image of a brain, the method comprising:
acquiring a 3D scout image;

selecting a plurality of axial working sections and a plurality of coronal working sections in the 3D scout image;

obtaining a set of axial reference lines and a set of coronal reference lines from the selected plurality of axial working sections and the selected plurality of coronal working sections, respectively;

filtering, from the set of axial reference lines and the set of coronal reference lines, a set of lines which are incompatible in a direction with a generalized vector having a direction of all lines in the set of axial reference lines and the set of coronal reference lines;

constructing at least one mid-sagittal plane of the brain based on the set of axial reference lines and the set of coronal reference lines;

detecting at least one landmark that is an anatomical point in the at least one mid-sagittal plane;

creating a first reference line based on the at least one landmark detected in the at least one mid-sagittal plane; and planning a scan in an orientation based on the at least one mid-sagittal plane and the first reference line.

2. The method of claim 1, wherein the set of axial reference lines and the set of coronal reference lines are obtained by using a numerical criterion that is calculated based on pixels in the plurality of axial working sections and the plurality of coronal working sections, the pixels being selected by analysis of the 3D scout image and based on detection of traces of a longitudinal fissure of the brain in the plurality of axial working sections and the plurality of coronal working sections.

3. The method of claim 2, wherein the creating the first reference line comprises:

determining a detector for detecting a longitudinal fissure of the brain, the detector comprising a set of pixels that are used for calculating the numerical criterion at a position of the detector;

creating a binary mask defined by an area of a two-dimensional (2D) image of the brain in at least one of the plurality of axial working sections and the plurality of coronal working sections;

obtaining main axes of the binary mask;

selecting a working area for detecting the longitudinal fissure of the brain in the at least one of the plurality of axial working sections and the plurality of corona working sections based on a geometrical structure of the binary mask and setting at least one parameter for changing a position of the detector in the working area, wherein the at least one parameter comprises a range of at least one from among coordinates and an angle of rotation of the detector;

determining a desired position of the detector in the working area based on the numerical criterion; and calculating the first reference line in the working area based on a central axis of the detector at the desired position.

4. The method of claim 3, wherein the determining the detector for detecting the longitudinal fissure of the brain comprises detecting the longitudinal fissure of the brain in a form of a band having a discontinuous part, the discontinuous part being excluded for calculating the numerical criterion.

5. The method of claim 2, wherein the numerical criterion is calculated based on comparison between intensities of the pixels in the plurality of axial working sections and the plurality of coronal working sections and a predetermined threshold value.

6. The method of claim 2, wherein the numerical criterion is calculated based on a normalized weighted sum of intensities of the pixels.

7. The method of claim 2, wherein the numerical criterion is calculated based on a normalized weighted sum of intensities of pixels of which intensities are in a predefined range.

8. The method of claim 3, wherein the determining the detector comprises determining the detector based on detecting the longitudinal fissure of the brain at predefined positions of the detector.

9. The method of claim 3, wherein the determining the detector comprises determining the detector based on a bundle of a plurality of lines selected from among a set of secants that are substantially parallel with one another, and the detecting the longitudinal fissure of the brain is performed at predefined directions of secants of the set of scants.

10. The method of claim 1, wherein the constructing the at least one mid-sagittal plane of the brain based on the set of axial reference lines and the set of coronal reference lines comprises:

obtaining a vector having a generalized direction of axial reference lines of the set of axial reference lines;

obtaining boundary points of the axial reference lines of the set of axial reference lines based on points of intersection between lines providing borders of binary masks corresponding to the plurality of axial working sections;

obtaining a central point having coordinates determined based on averaged coordinates of the boundary points;

constructing a plane that is orthogonal to the vector and passes through the central point;

determining points of intersection between the reference lines of the set of axial reference lines and creating a set of the points of intersection;

constructing a reference line based on a regression straight line passing through the set of the points of intersection; and constructing the at least one mid-sagittal plane based on a plane in which a normal vector is orthogonal to the vector and the reference line and passing through the central point.

11. The method of claim 1, wherein the constructing the at least one mid-sagittal plane of the brain based on the set of axial reference lines and the set of coronal reference lines comprises:

obtaining a first vector having a generalized direction of axial reference lines of the set of axial reference lines;

obtaining boundary points of the axial reference lines of the set of axial reference lines based on points of intersection between lines providing borders of binary masks corresponding to the plurality of axial working sections;

obtaining a central point having coordinates determined based on averaged coordinates of the boundary points;

constructing a plane that is orthogonal to the first vector and passes through the central point;

determining points of intersection between the reference lines of the set of axial reference lines and creating a set of the points of intersection;

constructing a reference line based on a regression straight line passing through the set of the points of intersection;

obtaining a second vector having a generalized direction of coronal reference lines of the set of coronal reference lines;

obtaining a third vector based on a weighted sum of the second vector and the reference line; and constructing the at least one mid-sagittal plane as a plane in which a normal vector is orthogonal to the first vector and the third vector and passing through the central point.

12. The method of claim 1, wherein the constructing the at least one mid-sagittal plane of the brain based on the set of axial reference lines and the set of coronal reference lines comprises:

obtaining boundary points that are points of intersection between lines in the set of axial reference lines and edges of binary masks corresponding to the plurality of axial working sections;

obtaining boundary points that are points of intersection between lines in the set of coronal reference lines and edges of binary masks corresponding to the plurality of coronal working sections; and obtaining the at least one mid-sagittal plane based on a regression plane comprising the boundary points using a least square method.

13. A non-transitory computer-readable storage medium storing a program for executing the method of claim 1 by a computer.

14. A system for automatically planning a view in a three-dimensional (3D) image of a brain, the system comprising:

a 3D scout image providing block configured to collect data of a medical image, and provide a 3D scout image from the data of the medical image;

a working section selection block configured to analyze the 3D scout image provided by the 3D scout image providing block, and select a plurality of axial working sections and a plurality of coronal working sections;

an axial section reference line calculation block configured to analyze the plurality of axial working sections selected by the working section selection block, detect traces of a longitudinal fissure of the brain in the plurality of axial working sections, and compute a set of axial reference lines based on central axial lines of the detected traces;

a coronal section reference line calculation block configured to analyze the plurality of coronal working sections selected by the working section selection block, detect traces of a longitudinal fissure of the brain in the plurality of coronal working sections, and compute a set of coronal reference lines based on central coronal lines of the detected traces;

an axial reference line filtration block configured to filter the set of axial reference lines computed by the axial section reference line calculation block by excluding, from the set of axial reference lines, lines whose direction vector differs from a vector having a generalized direction of the set of the axial reference lines by a predetermined degree, and provide a filtered set of axial reference lines;

a coronal reference line filtration block configured to filter the set of coronal reference lines computed by the coronal section reference line calculation block by excluding, from the set of coronal reference lines, lines whose direction vector differs from a vector having a generalized direction of the set of the coronal reference lines by the predetermined degree, and provide a filtered set of coronal reference lines;

a mid-sagittal plane (MSP) calculation block configured to provide a plane by applying a least square method to the filtered set of axial reference lines provided by axial reference line filtration block and the filtered set of coronal reference lines provided by the coronal reference line filtration block, and provide parameters of the plane;

an MSP image reconstruction block configured to provide an MSP image of the brain based on the parameters of the plane provided by the MSP calculation block and the 3D scout image provided by the 3D scout image providing block;

a landmark detection block configured to receive the MSP image of the brain provided by the MSP image reconstruction block, detect at least two landmarks of a predetermined type, and provide coordinates of the at least two landmarks;

a longitudinal reference line formation block configured to compute a longitudinal reference line based on the coordinates of the at least two landmarks provided by the landmark detection block, and provide parameters of the longitudinal reference line; and a view planning output interface block configured to transfer to a control system of a medical scanner the parameters of the plane provided by the MSP calculation block and the parameters of the longitudinal reference line provided by the longitudinal reference line formation block.

15. The system of claim 14, wherein at least one of the axial section reference line calculation block and the coronal section reference line calculation block comprises:

a binary mask formation block configured to receive a two-dimensional (2D) image of a working section, and compute a continuous binary mask defined by an image of the brain in the working section, and provide an image of the binary mask;

a main axis determination block configured to receive the image of the binary mask provided by the binary mask formation block, compute main axes of the binary mask, and transfer parameters of the main axes;

a working area determination block configured to analyze the parameters of the main axes provided by the main axis determination block, determine a working area for detecting a trace of a longitudinal fissure of the brain by a detector in the working section, determine a range of at least one from among horizontal movement and an angle of rotation of the detector at a test position, and provide the determined working area and the determined range;

a longitudinal fissure trace detection block configured to receive the determined working area and the determined range from the working area determination block, detect the longitudinal fissure of the brain in the working section corresponding to parameters of the working area, compute a predetermined range of positions of the detector, test the detector at a plurality of possible positions in the computed predefined range, calculate a criterion based on pixels included in the detector at each of the tested plurality of possible positions, compare values of the criterion for the tested plurality of positions of the detector, detect a desired position based on a result of the comparison, and provide geometrical parameters for the detected desired position of the detector; and a reference line calculation block configured to receive geometrical parameters of the optimum position of the detector provided by the longitudinal fissure trace detection block, and compute the reference line based on a central axis of the detector located at the desired position in the working section.

* * * * *